(12) United States Patent
Findley et al.

(10) Patent No.: US 10,017,346 B2
(45) Date of Patent: Jul. 10, 2018

(54) APPARATUS AND METHOD FOR LOADING MATERIAL USED IN THE MANUFACTURE OF ABSORBENT ARTICLES

(71) Applicant: The Procter & Gamble Company, Cincinnati, OH (US)

(72) Inventors: Daniel Patrick Findley, Finneytown, OH (US); Kazuaki Tameishi, Akashi (JP); Seiichi Ohide, Kakogawa (JP)

(73) Assignee: The Procter & Gamble Company, Cincinnati, OH (US)

( * ) Notice: Subject to any disclaimer, the term of this patent is extended or adjusted under 35 U.S.C. 154(b) by 624 days.

(21) Appl. No.: 14/690,531

(22) Filed: Apr. 20, 2015

(65) Prior Publication Data

US 2015/0298927 A1    Oct. 22, 2015

Related U.S. Application Data

(60) Provisional application No. 61/982,362, filed on Apr. 22, 2014.

(51) Int. Cl.
   *B65H 19/12*    (2006.01)
   *A61F 13/15*    (2006.01)
   *B65H 75/24*    (2006.01)

(52) U.S. Cl.
   CPC ..... *B65H 19/123* (2013.01); *A61F 13/15764* (2013.01); *B65H 75/248* (2013.01); *B65H 2801/57* (2013.01)

(58) Field of Classification Search
   CPC .............. B65H 19/123; B65H 75/248; B65H 2801/57; A61F 13/15764
   See application file for complete search history.

(56) References Cited

U.S. PATENT DOCUMENTS

| 3,565,361 A | 2/1971 | Merrill |
| 3,860,003 A | 1/1975 | Buell |

(Continued)

FOREIGN PATENT DOCUMENTS

| DE | 11 40 428 B | 11/1962 |
| DE | 35 33 735 A1 | 4/1987 |

(Continued)

OTHER PUBLICATIONS

13312 PCT International Search Report dated Jul. 24, 2015, 11 pages.

*Primary Examiner* — William A. Rivera
(74) *Attorney, Agent, or Firm* — Sarah M. DeCristofaro

(57) ABSTRACT

An apparatus and method for loading a spool, including a core and a web of material, on a loading apparatus and unwinding the web material from the core of the spool. The loading apparatus may include a mandrel adapted to be received by the core. The mandrel may include a tubular side wall having an outer circumferential surface, an inner circumferential surface, and an aperture. A gripping member may be telescopically received within the aperture. The gripping member may be configured to move radially outward to press against the core. Likewise, the gripping member may be configured to move radially inward to release the core. The loading apparatus may be configured to associate with an unwind apparatus. The unwind apparatus allows the loading apparatus to rotate about a central longitudinal axis. As the unwind apparatus rotates, the web of material may be unwound from the core of the spool.

26 Claims, 21 Drawing Sheets

(56) References Cited

U.S. PATENT DOCUMENTS

| | | | | |
|---|---|---|---|---|
| 4,142,690 A | * | 3/1979 | Karle | B65H 54/543 |
| | | | | 242/573.9 |
| 4,279,386 A | * | 7/1981 | Lobo | G11B 15/662 |
| | | | | 242/573.9 |
| 4,300,727 A | | 11/1981 | Koch et al. | |
| 4,496,114 A | * | 1/1985 | Kataoka | F16D 41/066 |
| | | | | 242/571.7 |
| 4,610,678 A | | 9/1986 | Weisman et al. | |
| 4,673,402 A | | 6/1987 | Weisman et al. | |
| 4,695,278 A | | 9/1987 | Lawson | |
| 4,704,115 A | | 11/1987 | Buell | |
| 4,715,553 A | * | 12/1987 | Hatakeyama | B65H 75/242 |
| | | | | 242/573.7 |
| 4,795,454 A | | 1/1989 | Dragoo | |
| 4,834,735 A | | 5/1989 | Alemany et al. | |
| 4,888,231 A | | 12/1989 | Angstadt | |
| 4,909,803 A | | 3/1990 | Aziz et al. | |
| 4,911,376 A | * | 3/1990 | Thompson | B65H 75/242 |
| | | | | 242/573.2 |
| 5,562,646 A | | 10/1996 | Goldman et al. | |
| 5,599,335 A | | 2/1997 | Goldman et al. | |
| 5,628,097 A | | 5/1997 | Benson et al. | |
| 5,669,894 A | | 9/1997 | Goldman et al. | |
| 5,771,807 A | * | 6/1998 | Moss | B41F 13/08 |
| | | | | 101/375 |
| 5,875,992 A | * | 3/1999 | Roder | B65H 75/185 |
| | | | | 242/573.4 |
| 5,916,661 A | | 6/1999 | Benson et al. | |
| 6,107,539 A | | 8/2000 | Palumbo et al. | |
| 6,545,197 B1 | | 4/2003 | Muller et al. | |
| 6,790,798 B1 | | 9/2004 | Suzuki et al. | |
| 7,044,418 B2 | * | 5/2006 | Leisten | B21C 47/04 |
| | | | | 242/539 |
| 7,569,039 B2 | | 8/2009 | Matsuda et al. | |
| 8,440,043 B1 | | 5/2013 | Schneider et al. | |
| 8,708,271 B2 | * | 4/2014 | Noll | B41F 17/002 |
| | | | | 242/573.3 |
| 2004/0097895 A1 | | 5/2004 | Busam et al. | |
| 2004/0158212 A1 | | 8/2004 | Ponomarenko et al. | |
| 2005/0107764 A1 | | 5/2005 | Matsuda et al. | |
| 2009/0312730 A1 | | 12/2009 | LaVon et al. | |
| 2012/0061015 A1 | | 3/2012 | LaVon et al. | |
| 2012/0061016 A1 | | 3/2012 | LaVon et al. | |
| 2013/0206894 A1 | | 8/2013 | Miyamoto et al. | |
| 2013/0255861 A1 | | 10/2013 | Schneider | |
| 2013/0255862 A1 | | 10/2013 | Schneider et al. | |
| 2013/0255863 A1 | | 10/2013 | LaVon et al. | |
| 2013/0255864 A1 | | 10/2013 | Schneider et al. | |
| 2013/0255865 A1 | | 10/2013 | Brown et al. | |

FOREIGN PATENT DOCUMENTS

| | | |
|---|---|---|
| DE | 43 35 259 A1 | 4/1995 |
| EP | 1 795 469 A1 | 6/2007 |
| JP | 11-246086 | 9/1999 |
| JP | 2013-112487 | 6/2013 |

* cited by examiner

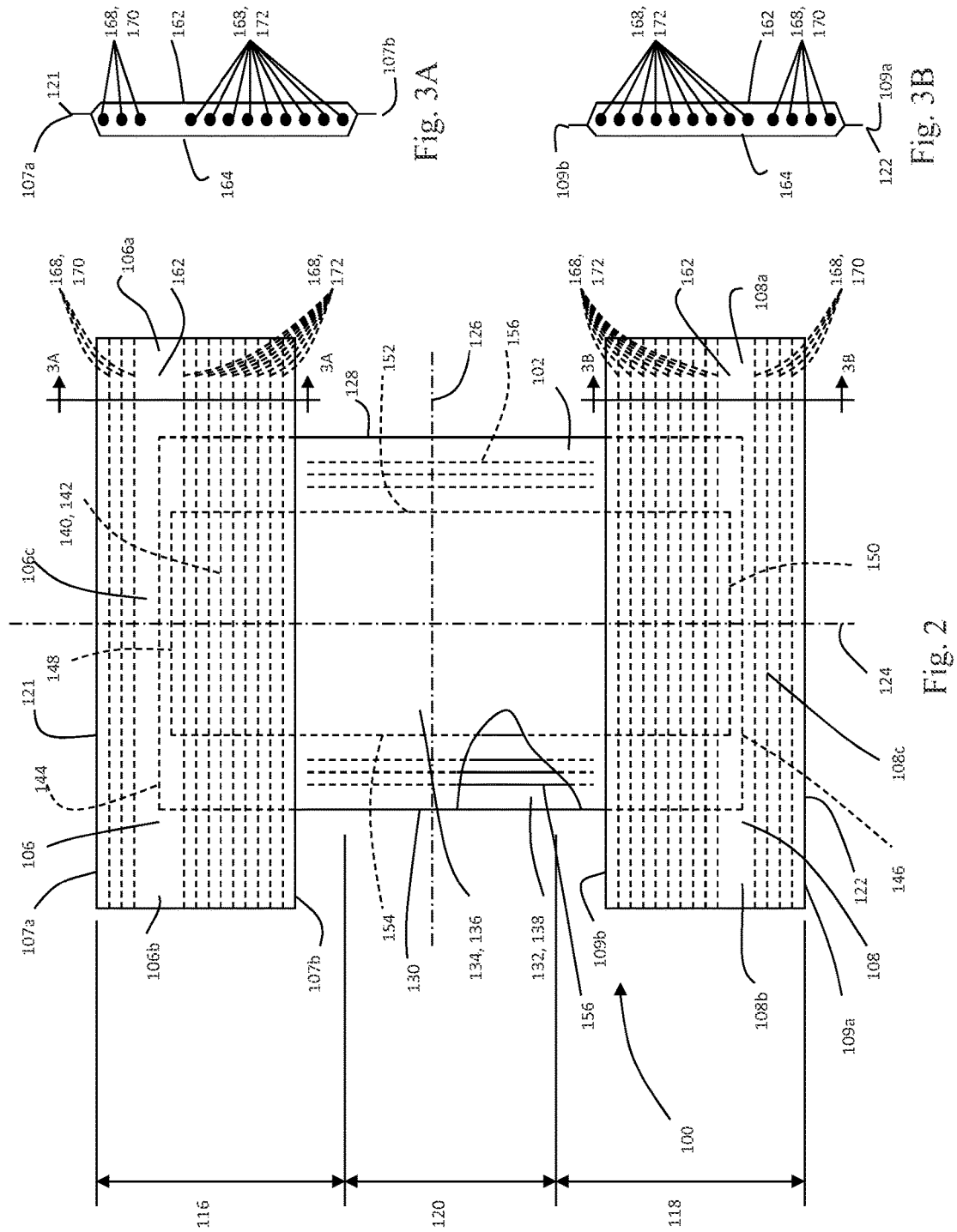

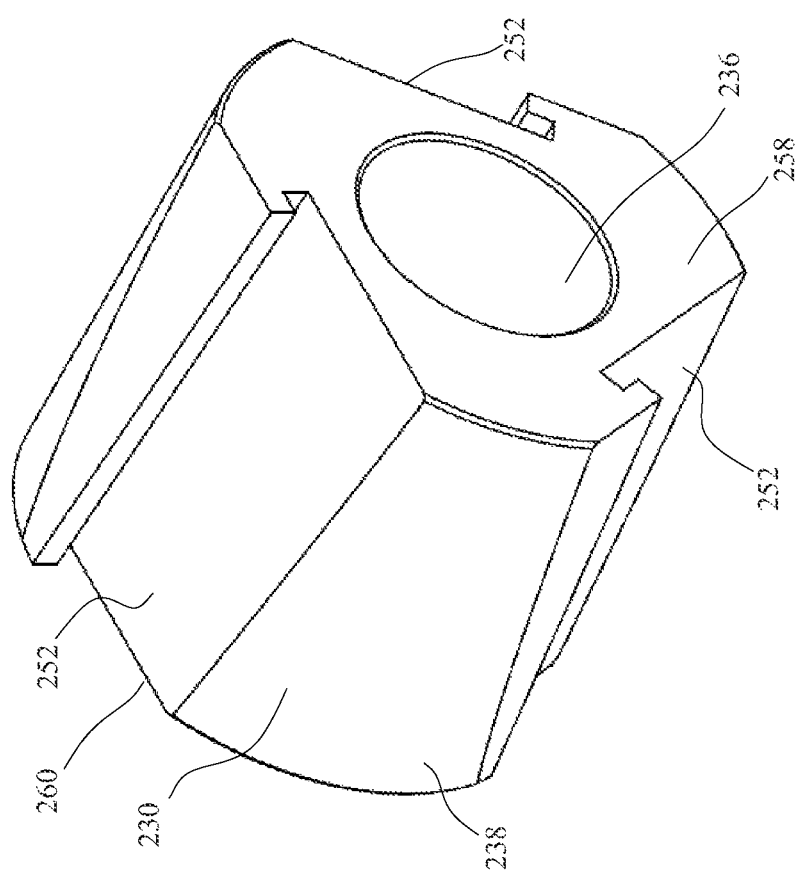

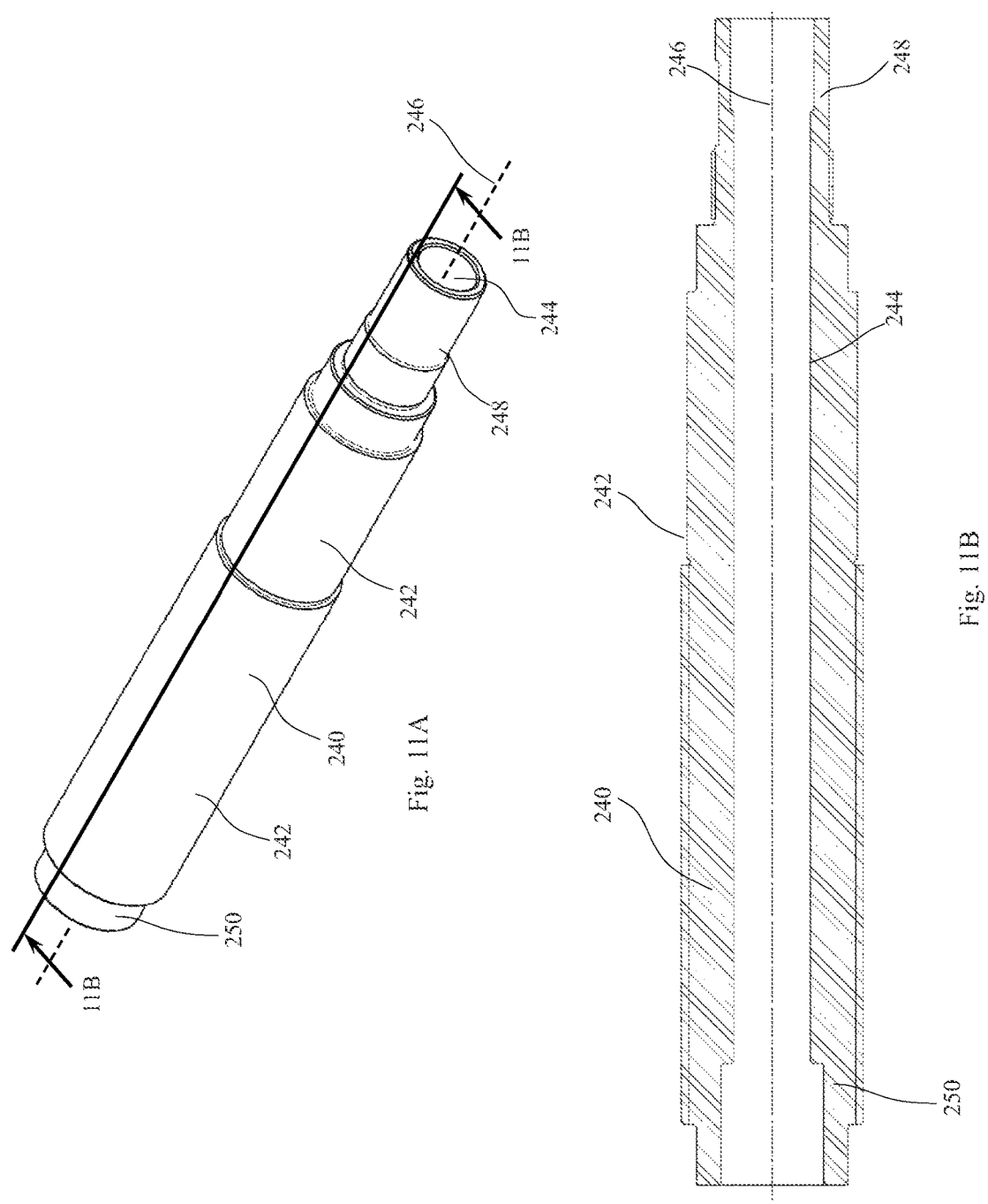

APPARATUS AND METHOD FOR LOADING MATERIAL USED IN THE MANUFACTURE OF ABSORBENT ARTICLES

CROSS REFERENCE TO RELATED APPLICATIONS

This application claims the benefit of U.S. Provisional Application No. 61/982,362, filed Apr. 22, 2014, which is herein incorporated by reference in its entirety.

FIELD OF THE INVENTION

The present disclosure relates to apparatuses and methods for manufacturing absorbent articles, and more particularly, to apparatuses and methods for loading material used in absorbent articles.

BACKGROUND OF THE INVENTION

Along an assembly line, diapers and various types of other absorbent articles may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheets, absorbent cores, front and/or back ears, fastener components, and various types of webs and components such as leg elastics, barrier leg cuff elastics, and waist elastics. Once the desired component parts are assembled, the advancing web(s) and component parts are subjected to a final knife cut to separate the web(s) into discrete diapers or other absorbent articles. The discrete diapers or absorbent articles may also then be folded and packaged.

As mentioned above, during the assembly process, various continuous webs of material are used to manufacture diapers. Generally, these webs of material are supplied on spools that comprise a core and a web material wound around the core. For example, films and elastics may be wound about the core to comprise a spool. Typically, the diameter of the core is relatively small in comparison to the diameter of the material wound about the core. Thus, spools are often prone to becoming misaligned when being handled. Stated another way, the material wound about the core may easily become spirally displaced such that the material farthest from the core is not in line with the material wound about the surface of the core. Thus, the side of the spool fails to be a substantially planar surface. In addition to the general structure of the spool, the need for operators to handle spools also increases the risk of placing a spirally displaced spool on the manufacturing line. Due to the relatively large amount of material used in manufacturing absorbent articles, the spools are handled frequently by operators. For example, operators are often required to remove the spools from the storage container, mount the spool on the unwind mandrel, and push the spool into the proper location for unwind. Thus, there are relatively numerous opportunities for the spool to become spirally displaced. Placing a spool that has undergone some degree of displacement may lead to a disruption in material fed to the manufacturing line that may result in, for example, defective products and manufacturing down time.

Thus, a need exists for a method and an apparatus that reduces the potential of having a spirally displaced spool loaded on the unwind device and reduces the potential for disruption in the material being supplied to the manufacturing line.

SUMMARY OF THE INVENTION

Aspects of the present disclosure relate to an apparatus and method for assembling absorbent articles. The apparatus may include a loading apparatus for supporting a spool comprising a core and a web of material wound around the core. The apparatus may include a mandrel adapted to be received by the core. The mandrel may include a tubular side wall extending longitudinally between a first end portion and a second end portion. The tubular side wall may include an outer circumferential surface, an inner circumferential surface, and an aperture. The aperture may be configured to telescopically receive a gripping member. The gripping member may include a first surface and a second surface. The first surface may face radially outward from the tubular side wall. The apparatus may also include a wedge member slidably associated with the second surface of the gripping member. The wedge member may be received within the mandrel and may be adapted to move longitudinally along the inner circumferential surface of the tubular side wall. As the wedge member moves longitudinally in a first direction, the first surface of the gripping member may move radially outward to press against the core. Likewise, as the wedge member moves longitudinally in a second direction opposite the first direction, the first surface of the gripping member may move radially inward to release the core.

In another embodiment, a method for loading a spool on an unwind device may include the steps of: providing a mandrel comprising a tubular side wall extending longitudinally between a first end portion and a second end portion, the tubular side wall including an outer circumferential surface and an inner circumferential surface; retracting a gripping member radially inward through an aperture in the tubular side wall of the mandrel by moving a wedge member in a first direction longitudinally along the inner circumferential surface of the tubular side wall of the mandrel; providing a spool comprising a core and a web of material wound around the core; inserting the mandrel into the core; projecting the gripping member radially outward through the aperture in the tubular side wall of the mandrel to grip the core by moving a wedge member in a second direction longitudinally along the inner circumferential surface of the tubular side wall, wherein the second direction opposite the first direction; and releasing the core by moving the wedge member longitudinally along the inner circumferential surface of the tubular side wall in the second direction.

BRIEF DESCRIPTION OF THE DRAWINGS

FIG. 2 is a partially cut away plan view of the diaper pant shown in FIG. 1;

FIG. 3A is a cross-sectional view of the diaper pant of FIG. 2 taken along line 3A-3A in accordance with one non-limiting embodiment of the present disclosure;

FIG. 3B is a cross-sectional view of the diaper pant of FIG. 2 taken along line 3B-3B in accordance with one non-limiting embodiment of the present disclosure;

FIG. 9A is a perspective view of a wedge member in accordance with one non-limiting embodiment of the present disclosure;

FIG. 11A is a perspective view of an outer shaft in accordance with one non-limiting embodiment of the present disclosure;

FIG. 11B is a cross-sectional view of the outer shaft of FIG. 11A taken along line 11B-11B in accordance with one non-limiting embodiment of the present disclosure;

DETAILED DESCRIPTION OF THE INVENTION

Figure 1:
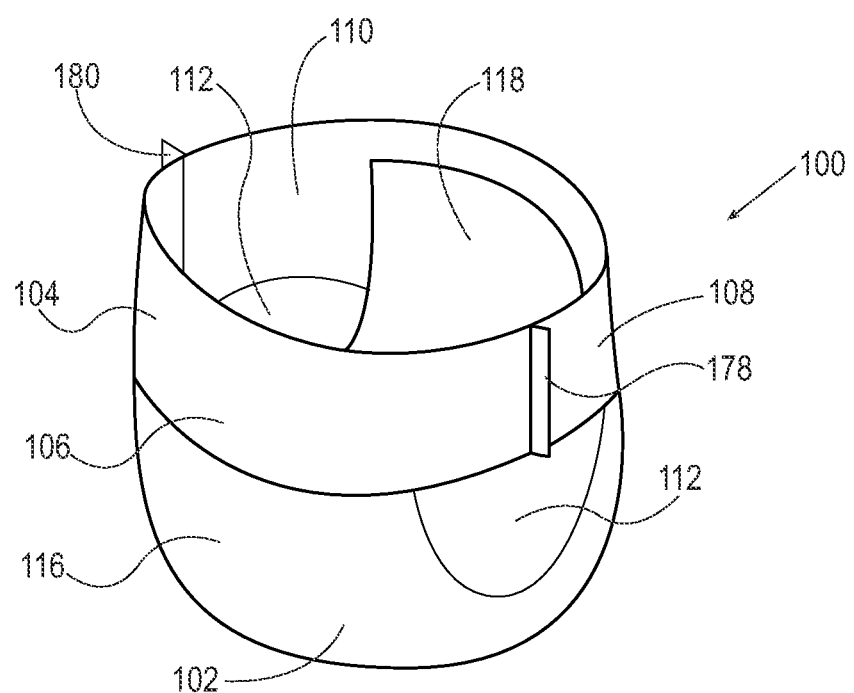
FIG. 1 is a perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant may be configured with a continuous or closed waist opening and at least one continuous, closed, leg opening prior to the article being applied to the wearer.

The term "machine direction" (MD) is used herein to refer to the direction of material flow through a process. In addition, relative placement and movement of material may be described as flowing in the machine direction through a process from upstream in the process to downstream in the process.

The present disclosure relates to a method and apparatus for loading spools of material for use in absorbent articles. More particularly, the apparatus herein is directed to an apparatus for loading and unwinding a spool of material, such as a stranded elastic, film, or other similar web of material used in the manufacture of absorbent articles. As discussed in more detail below, the loading apparatus may include a mandrel adapted to support a spool of material. The loading apparatus may further include a gripping member than may extend radially outward from the mandrel to engage the core of the spool. The gripping member hold the spool on the mandrel during transport and loading of the spool onto an unwind apparatus. The loading apparatus may be configured to engage with a portion of the unwind apparatus. The unwind apparatus may include a mount member onto which the mandrel may be removably connected. More specifically, the unwind apparatus may include a bracing member configured to protrude through an aperture in the mount member and to engage and hold the mandrel. As discussed in more detail below, the unwind apparatus and the loading apparatus may be reconfigurable. For example, in a first configuration, the loading apparatus may be connected with the unwind apparatus such that a spool may be unwound. In a second configuration, the loading apparatus may be disconnected with the unwind apparatus, and the mandrel may support one or more spools of material.

It is to be appreciated that various arrangements and configurations of the apparatus herein may be used to load and unwind various types of materials used in various articles of manufacture. For example, as discussed in more detail below, the apparatus according to the present disclosure may be utilized in the production of various components of absorbent articles, such as diapers. To help provide additional context to the subsequent discussion of the process embodiments, the following provides a general description of absorbent articles in the form of diapers that include components including the materials that may be used by the methods and apparatuses discussed herein.

FIGS. 1 and 2 show an example of a diaper pant 100 that may be assembled with the apparatuses and methods discussed herein. In particular, FIG. 1 shows a perspective view of a diaper pant 100 in a pre-fastened configuration, and FIG. 2 shows a plan view of the diaper pant 100 with the portion of the diaper that faces away from a wearer oriented towards the viewer. The diaper pant 100 shown in FIGS. 1 and 2 includes a chassis 102 and a ring-like elastic belt 104. As discussed below in more detail, a first elastic belt 106 and a second elastic belt 108 are connected together to form the ring-like elastic belt 104.

With continued reference to FIG. 2, the chassis 102 includes a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region 120 may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIG. 2 is shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1 and 2, the diaper pant 100 may include an inner, body facing surface 132, and an outer, garment facing surface 134. The chassis 102 may include a backsheet 136 and a topsheet 138. The chassis 102 may also include an absorbent assembly 140 including an absorbent core 142 that may be disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. As shown in FIG. 2, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. Moreover, the crotch region 120 may be generally positioned between the legs of the wearer with the absorbent core 142 extending from the front waist region 116 through the crotch region 120 to the back waist region 118.

It is also to be appreciated that a portion or the whole of the diaper 100 may also be made laterally extensible. The additional extensibility may help allow the diaper 100 to conform to the body of a wearer during movement by the wearer. The additional extensibility may also help, for example, allow the user of the diaper 100 including a chassis 102 having a particular size before extension to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas, and undergarments. The backsheet 136 may also include a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also include an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

The diaper pant 100 may also include an absorbent assembly 140 that is joined to the chassis 102. As shown in FIG. 2, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

The diaper 100 may also include elasticized leg cuffs 156. It is to be appreciated that the leg cuffs 156 may be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; U.S. Patent Publication No. 2009/0312730A1; and U.S. Patent Publication No. 2013/0255865A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1. As previously mentioned, the ring-like elastic belt 104 is defined by a first elastic belt 106 connected with a second elastic belt 108. As shown in FIG. 2, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 121 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts may include a nonwoven web of synthetic fibers, and may include a stretchable nonwoven. In other embodiments, the first and second elastic belts may include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2, 3A, and 3B, the belt elastic material may include a plurality of elastic strands 168 that may be referred to herein as outer, waist elastics 170 and inner, waist elastics 172.

As shown in FIG. 2, the outer, waist elastics 170 extend continuously laterally between the first and second opposing end regions 106a, 106b and across the central region 106c of the first elastic belt 106 and between the first and second opposing end regions 108a, 108b and across the central region 108c of the second elastic belt 108. In some embodiments, some elastic strands 168 may be configured with discontinuities in areas. For example, as shown in FIG. 2, the inner, waist elastics 172 extend intermittently along the first and second elastic belts 106, 108. More particularly, the inner, waist elastics 172 extend along the first and second opposing end regions 106a, 106b and partially across the central region 106c of the first elastic belt 106. The inner, waist elastics 172 also extend along the first and second opposing end regions 108a, 108b and partially across the central region 108c of the second elastic belt 108. As such, the inner, waist elastics 172 do not extend across the entirety of the central regions 106c, 108c of the first and second elastic belts 106, 108. Thus, some elastic strands 168 may not extend continuously through regions of the first and second elastic belts 106, 108 where the first and second elastic belts 106, 108 overlap the absorbent assembly 140. In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2.

As previously mentioned, the apparatuses and methods according to the present disclosure may be utilized to assemble discrete absorbent articles 100 and/or various components of absorbent articles 100, such as for example, chassis 102, elastic belts 106, 108, and/or leg cuffs 156. Although the following methods may be provided in the context of the diaper 100 shown in FIGS. 1 and 2, it is to be appreciated that the methods and apparatuses herein may be used with various process configurations and/or absorbent articles, such as for example, disclosed in U.S. Pat. No. 7,569,039; U.S. Patent Publication Nos. 2005/0107764A1, 2012/0061016A1, and 2012/0061015A1; 2013/0255861A1; 2013/0255862A1; 2013/0255863A1; 2013/0255864A1; and 2013/0255865A1, all of which are incorporated by reference herein.

The apparatuses and methods according to the present disclosure may be utilized to supply material, such as elastics, to assemble laminates, such as elastic laminates, that may be used in various components of absorbent articles, such as for example, elastic belts 106, 108 and/or leg cuffs 156. Such elastic laminates may be assembled by positioning the supplied elastic material between two or more substrate layers. It is to be appreciated that the elastic laminates may be constructed in various ways, such as for example, in accordance with the methods and apparatuses disclosed in U.S. Pat. No. 8,440,043 and U.S. Patent Publication Nos. 2013/0255861A1; 2013/0255862A1; 2013/0255863A1; 2013/0255864A1; and 2013/0255865A1, which are all incorporated by reference herein. Although the following methods may be provided in the context of the diaper 100 shown in FIGS. 1 and 2, it is to be appreciated that elastic laminates may be used with various embodiments of diapers manufactured according the methods disclosed herein, such as for example, the absorbent articles disclosed in U.S. Pat. No. 7,569,039, filed on Nov. 10, 2004; U.S. Patent Publication No. 2005/0107764A1, filed on Nov. 10, 2004; U.S. Patent Publication No. 2012/0061016, filed on Aug. 30, 2011; and U.S. Patent Publication No. 2012/0061015, filed on Aug. 30, 2011, which are all hereby incorporated by reference herein.

Figure 4:
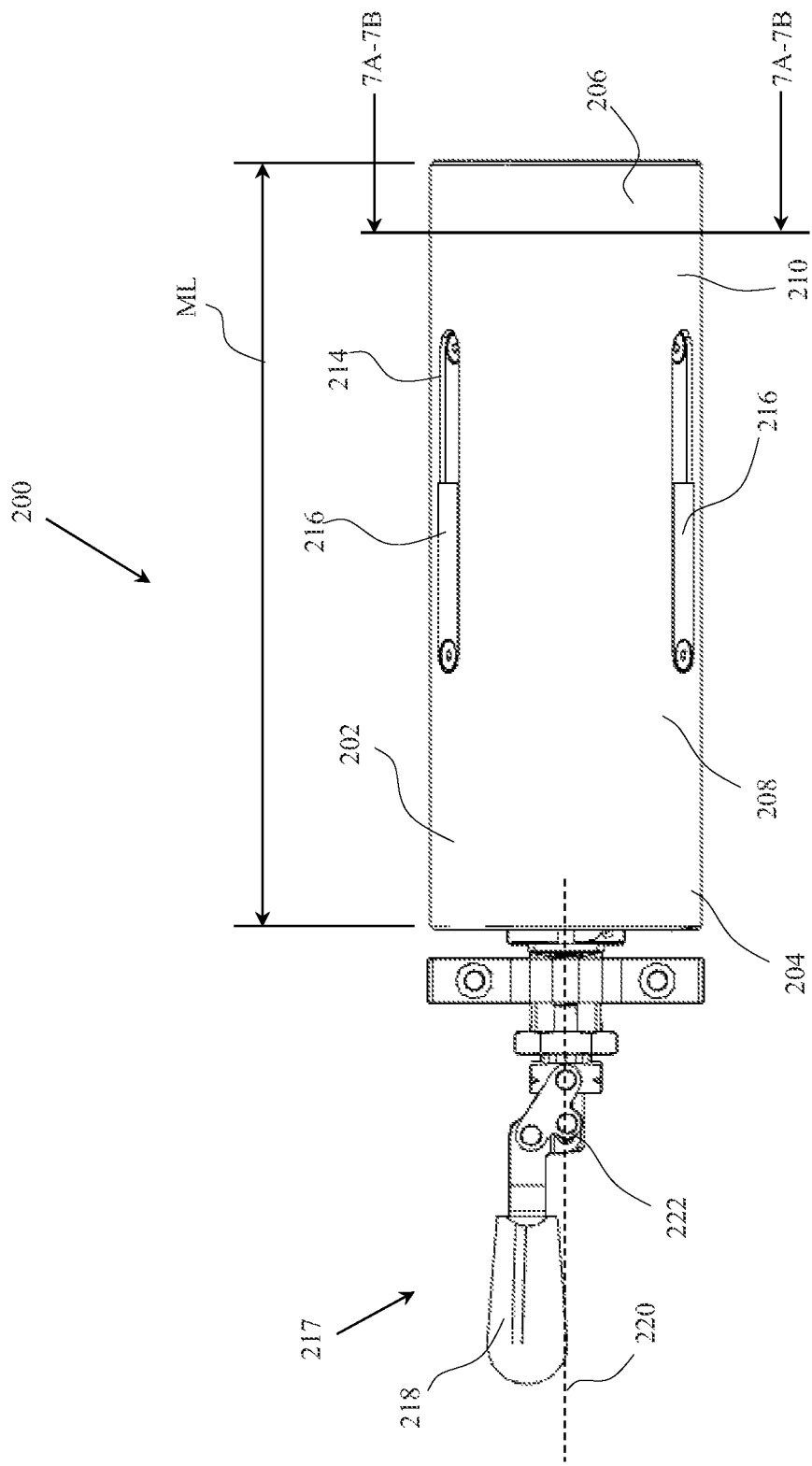
FIG. 4 is a side view of a loading apparatus in accordance with one non-limiting embodiment of the present disclosure.
Figure 5:
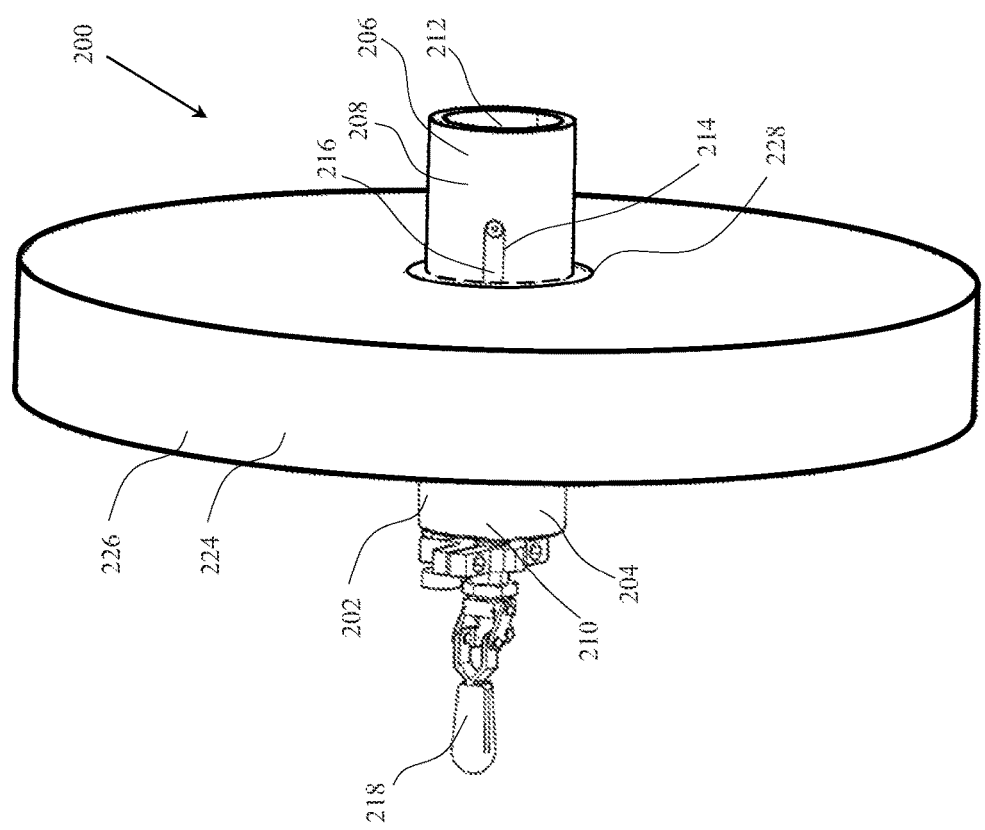
FIG. 5 is a perspective view of a loading apparatus including a spool in accordance with one non-limiting embodiment of the present disclosure.

FIGS. 4 and 5 show an embodiment of a loading apparatus 200 that may be used to load a spool 224 used in the manufacture of an absorbent article 100. The spool 224 may include a core 228 and a web of material 226 wound about the core 228. As shown, the loading apparatus may include a mandrel 202 that may be configured to support the spool 224. The mandrel 202 has a mandrel length ML. The mandrel length ML may be long enough to support at least one spool 224, as shown in FIG. 5. In some example embodiments, the mandrel length ML may be from about 100 mm to about 1 m and/or from about 125 mm to about 700 mm and/or from about 200 mm to about 500 mm and/or from about 215 mm to about 350 mm, including all 0.1 increments therebetween. The mandrel 202 may include a tubular side wall 208 having a first end portion 204 and a second end potion 206 opposite the first end portion. When the spool 224 has been loaded onto the mandrel 202, the core 228 of the spool 224 may substantially surround at least a portion of the tubular side wall 208 of the mandrel 202 and may be positioned between the first end portion 204 and the second end portion 206 of the mandrel 202. Further, the tubular side wall 208 may also define an aperture 214. The aperture 214 may be configured to receive a gripping member 216. More specifically, the gripping member 216 may be telescopically received within the aperture 214. Thus, the gripping member 216 may move radially outward and radially inward with respect to the aperture 214 defined by the tubular side wall 208. This may allow the gripping member 216 to engage and/or disengage the core 228 of the spool 224. Once the spool 224 has been loaded onto the mandrel 202, the gripping member 216 may move radially outward to engage the core 228 of the spool 224, which, in other words, may hold the spool 224 in place while an operator moves the spool 224, for example, from a storage container to the manufacturing line. Generally, the movement of the gripping member 216 may be controlled by the clamp member 217, as will be explained in greater detail herein. The clamp member 217 may include a handle 218 that may be rotatable about a central handle axis 220 and may pivot about a pivot point 222.

Figure 6:
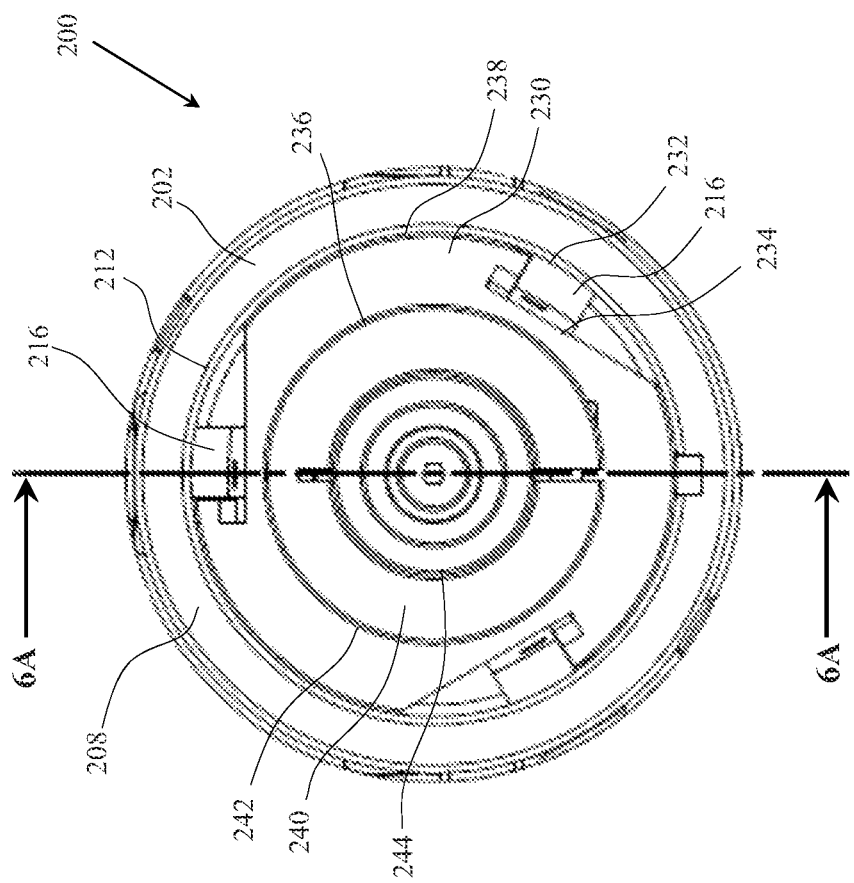
FIG. 6 is an end view of a loading apparatus in accordance with one non-limiting embodiment of the present disclosure.
Figure 6A:
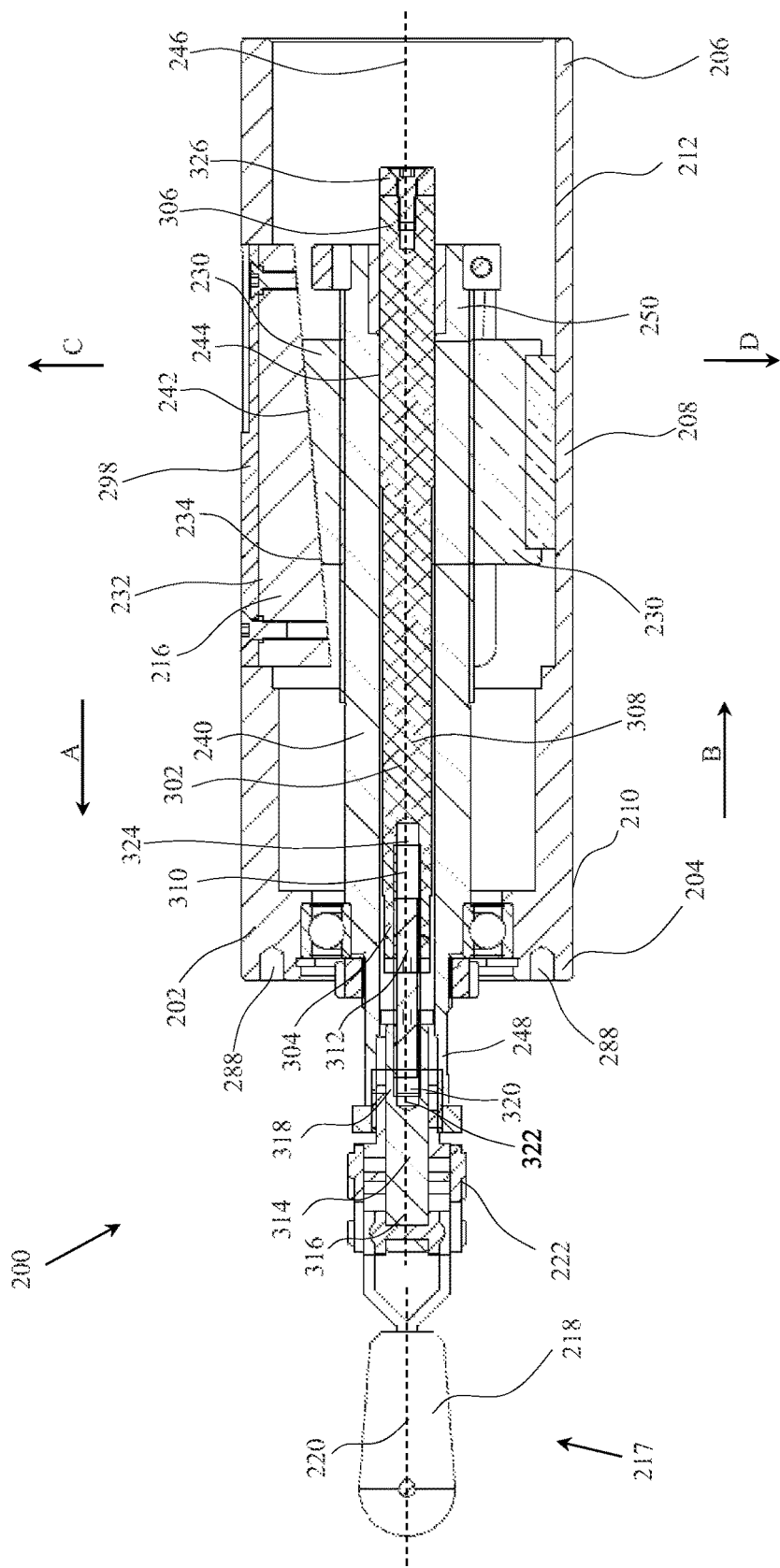
FIG. 6A is a side view of a cross-section of a loading apparatus of FIG. 6 taken along line 6A-6A in accordance with one non-limiting embodiment of the present disclosure.

As mentioned above, the gripping member 216 may be telescopically received within the aperture 214 of the mandrel 202. Referring to FIGS. 6 and 6A, the gripping member 216 may include a first surface 232 and a second surface 234. The first surface 232 of the gripping member 216 faces radially outward from the tubular side wall 208. The second surface 234 of the gripping member 216 may be slidably associated with a wedge member 230. The wedge member 230 may be received within the mandrel 202 and configured to move longitudinally along the inner circumferential surface 212 of the tubular side wall 208 of the mandrel 202. Generally, when the wedge member 230 moves longitudinally in a first direction, as indicated by arrow A, the first surface 232 of the gripping member 230 may move radially outward, as indicated by arrow C, so that first surface 232 may press against the core 228 of the spool 224. Similarly, when the wedge member 230 moves longitudinally in a second direction, as indicated by arrow B, which may be opposite the first direction, the first surface 232 of the gripping member 230 may move radially inward, as indicated by arrow D, so that the core 228 may be released. Further, the second surface 234 of the gripping member 216 may maintain engagement with the wedge member 230 as the wedge member 230 moves in the first direction and the second direction. It is to be appreciated that the first direction and the second direction may be reversed, such that the first direction is indicated by arrow B and the second direction is indicated by arrow A.

To move the wedge member 230 along the inner circumferential surface 212 of the tubular side wall 208 of the mandrel 202, the wedge member 230 may be slidably associated with an outer shaft 240. The wedge member 230 may include an internal wedge surface 236 and an external wedge surface 238. The external wedge surface 238 may be engaged with the second surface 234 of the gripping member 216. The internal wedge surface 236 may be engaged with an external surface 242 of the outer shaft 240. In some example embodiments, the internal wedge surface 236 may include one or more threads and the external surface 242 of the outer shaft 240 may include one or more threads. Thus, the internal wedge surface 236 may be threadably engaged with the external surface 242 of the outer shaft 240. Further, the outer shaft 240 may rotate about a central longitudinal axis 246. As the outer shaft 240 rotates about the central longitudinal axis 246, the threads disposed on the internal wedge surface 236 may associate with the threads of the external surface 242 of the outer shaft 240 resulting in the wedge member 230 advancing longitudinally in a first direction or a second direction, which may depending on the direction of rotation of the outer shaft 240.

It is to be appreciated that in some embodiments, the external surface 242 of the outer shaft 240 may include splines, which may be ridges that protrude from the external surface 242 of the outer shaft 240, and the internal wedge surface 236 may include a mating spline surface, which may be grooves, to receive the splined outer shaft 240. The spline on the external surface 242 of the outer shaft 240 may transfer torque to the groove on the internal wedge surface 236 allowing the outer shaft 240 to rotate and the wedge member 230 to move longitudinally along to the inner circumferential surface 210 of the mandrel 202. The splined surface may be, for example, linear or curved. Similarly, the mating splined surface may be linear or curved. The shape of the splined surface and the mating splined surface should be such that the torque of the rotating outer shaft 240 can be transferred to the wedge member 230, which may result in the wedge member 230 advancing along the inner circumferential surface 212 of the mandrel 202. In some embodiments, the outer shaft 240 may include the mating splined surface and the internal wedge surface 236 may include the splined surface.

The outer shaft 240 may further include a proximal end portion 248 and a distal end portion 250, opposite the proximal end portion 248. Adjacent the proximal end portion 248 of the outer shaft 240 may be the clamp member 217 including a handle member 218. In some example embodiments, the clamp member 217 may be connected to at least a portion of the proximal end portion 248 of the outer shaft 240. Further, as previously mentioned, the handle member 218 may be rotatable about the central handle axis 220. Thus, as an operator rotates the handle member 218, the handle member 218 may operatively engage the outer shaft 240 resulting in rotation of the outer shaft 240 about the central longitudinal axis 246. In some embodiments, the outer shaft 240 may be mechanically and/or chemically connected to a portion of the clamp member 217. More specifically, for example, the outer shaft 240 may be connected to the clamp member 217 by screws, clamps, adhesives, or other similar connection means. In some embodiments, the outer shaft 240 and the clamp member 217 may be manufactured such that the outer shaft 240 forms a frictional fit over a portion of the clamp member 217.

In summary, an operator may load a spool 224 onto the mandrel 202. Once the spool 224 has been loaded, the operator may rotate the handle member 218 of the clamp member 217. The clamp member 217 may operatively engage the outer shaft 240 resulting in rotation of the outer shaft 240 about the central longitudinal axis 246. The rotation of the outer shaft 240 may cause the wedge member 230 to move longitudinally in at least one of a first direction and a second direction. When the wedge member 230 moves longitudinally in a first direction, the first surface 232 of the gripping member 216 may move radially outward through the aperture 214 in the tubular side wall 208 of the mandrel 202. The gripping member 216 may engage a core 228 of a spool 224, which may hold the spool 224 in position during transport or any other movement that may occur prior to loading the spool in position for unwinding. Similarly, when the wedge member 230 moves longitudinally in a second direction, the first surface 232 of the gripping member 216 may move radially inward through the aperture 214 of the tubular side wall 208 of the mandrel 202. The gripping member 216 may disengage the core 228 of the spool 224, which may release the core 228 such that the core 228 is moveable along the tubular side wall 208 of the mandrel 202.

Figure 7B:
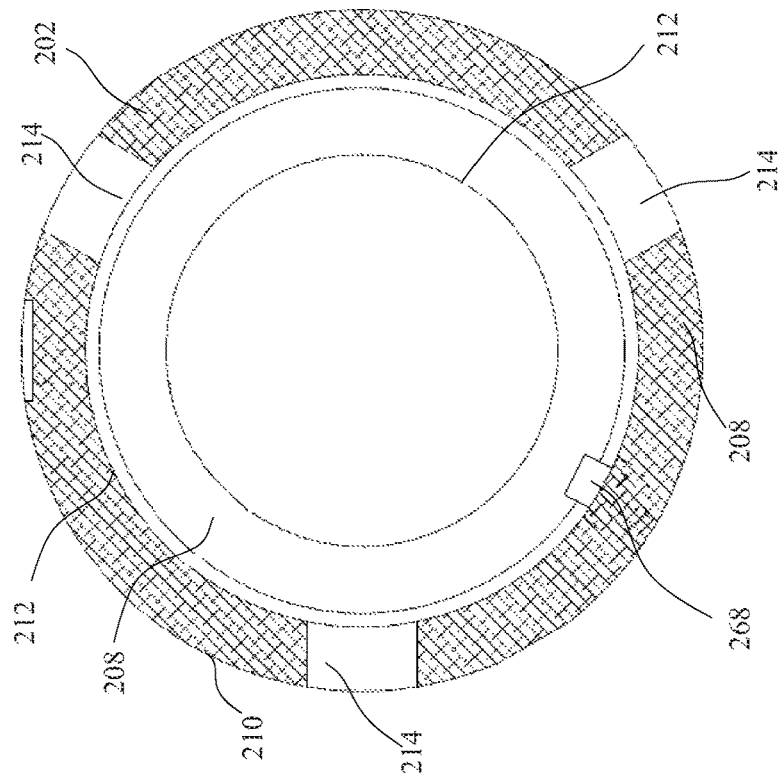
FIG. 7B is an end view of a mandrel in accordance with one non-limiting embodiment of the present disclosure.
Figure 7A:
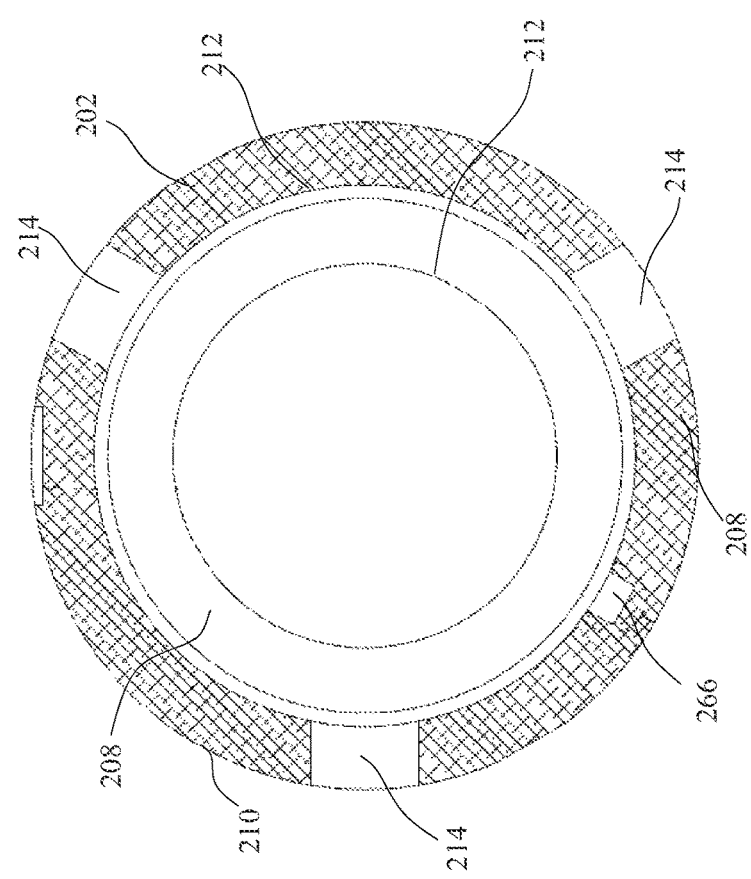
FIG. 7A is an end view of a mandrel in accordance with one non-limiting embodiment of the present disclosure.

In view of the aforementioned, each component of the loading apparatus 200 is herein discussed in more detail. FIGS. 7A and 7B illustrate an end view of the mandrel 202. The mandrel 202 may include a tubular side wall 208 having an outer circumferential surface 210 and an inner circumferential surface 212. The outer circumferential surface 210 may be sized to accept the core 228 of the spool 224. In some example embodiments, the outer circumferential surface 210 may have a diameter from about 50 mm to about 300 mm and/or from about 60 mm to about 200 mm and/or about 70 mm to about 100 mm, including all 0.1 mm therebetween. Further, the tubular side wall 208 may define an aperture 214 configured to telescopically receive the gripping member 216.

Figure 10B:
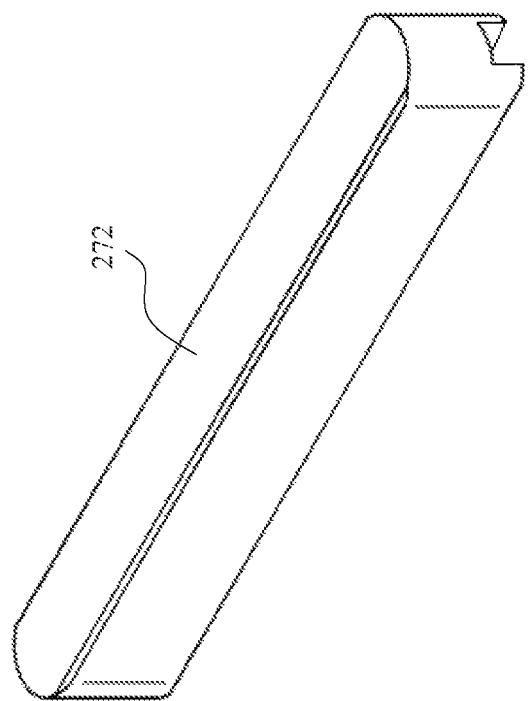
FIG. 10B is a perspective view of a key in accordance with one non-limiting embodiment of the present disclosure.
Figure 10A:
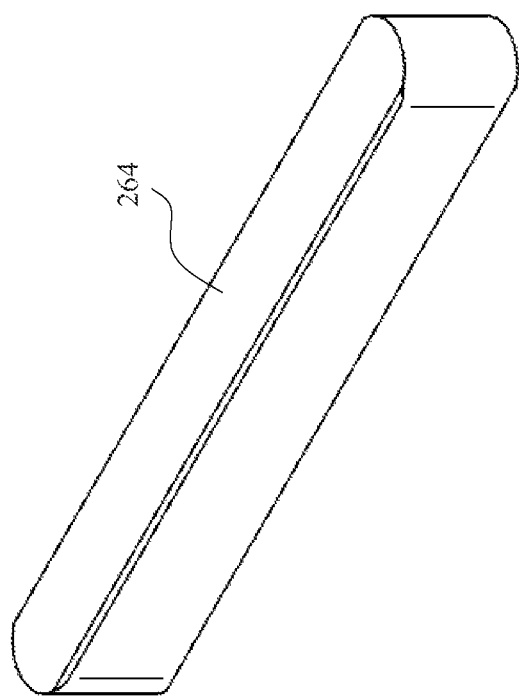
FIG. 10A is a perspective view of a key in accordance with one non-limiting embodiment of the present disclosure.

The tubular side wall 208 may also include a groove 266, as illustrated in FIG. 7A. The groove 266 may be configured to associate with a block key 264, as shown in FIG. 10A. The block key 264 may be slidably engaged with the groove 266. Stated another way, the block key 264 may move longitudinally within the groove 266. The groove 266 may be used to prevent the wedge member 230 from rotating with the outer shaft 240 and to guide the movement of the wedge member 230 in a longitudinal direction.

In some embodiments, the tubular side wall 208 may include a ridge 268, as illustrated in FIG. 7B. The ridge may be configured to associate with at least one of a groove key 272, as illustrated in FIG. 10B, and the wedge member 230. Stated another way, the groove key 272 and/or the wedge member 230 may be configured to receive the ridge 268 such that the ridge is slidably engaged with the groove key 272 and/or the wedge member 230. The ridge 268 may be used to prevent the wedge member 230 from rotating with the outer shaft 240 and to guide the movement of the wedge member 230 in a longitudinal direction. It is to be appreciated that a key may be any shape such that it is configured to engage the tubular side wall 208 and prevent rotation of the wedge member 230.

Figure 8A:
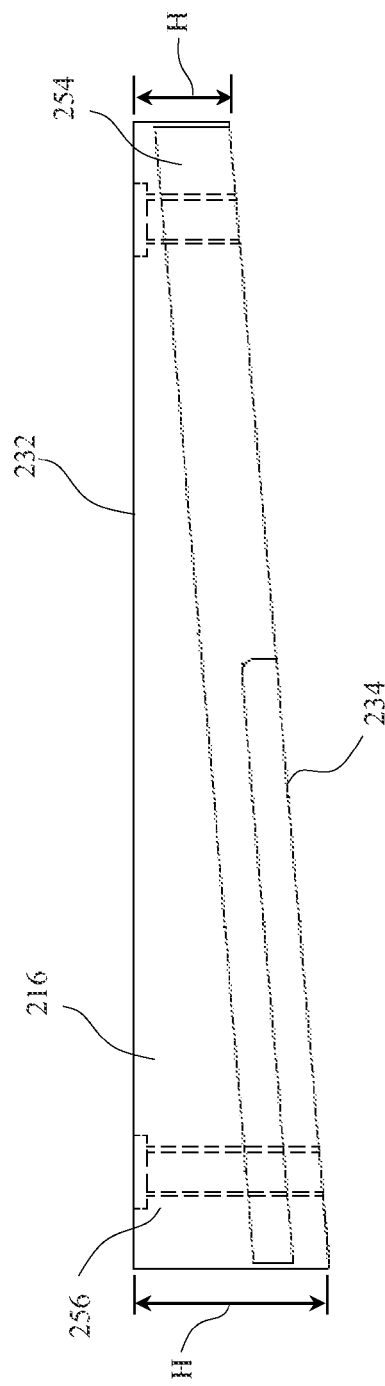
FIG. 8A is a side view of a gripping member in accordance with one non-limiting embodiment of the present disclosure.
Figure 8B:
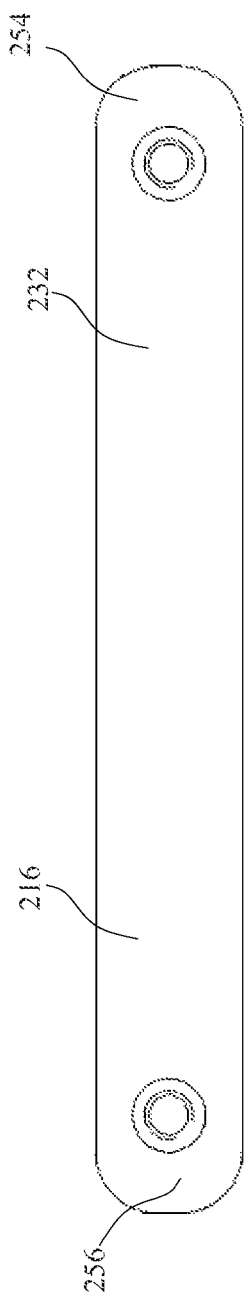
FIG. 8B is a top view of a gripping member in accordance with one non-limiting embodiment of the present disclosure.

As illustrated in FIGS. 8A and 8B, the gripping member 216 may include a first surface 232, a second surface 234, a first end portion 254, and a second end portion 256, opposite the first end portion 254. In some embodiments, the first surface 232 may be a substantially planar surface. The substantially planar surface of the first surface 232 may allow the gripping member 216 to engage a greater surface area of the core 228. However, it is to be appreciated that other profiles of the first surface 232 may be better suited to engage the core 228. Further, the surface profile of the first surface 232 may be designed and/or chosen with the surface profile of the core 228 in mind. Thus, the first surface 232 may engage the core 228 so that the gripping member 216 is able to hold the core 228 during transportation and/or unwinding of the spool 224. For example, the first surface 288 of the gripping member 216 may engage the core 228 and hold the core 228 due to the frictional force between the first surface 288 and the core 228. The surface profile of the first surface 232 may be designed to increase the frictional force when engaged with the core 228.

In some embodiments, the gripping member 216 may be associated with a surface member 298, as shown in FIG. 6A. The surface member 298 may include a certain surface profile that coordinates with the profile of the core 228. The surface member 298 may be removably connected to the first surface 232 of the gripping member 216. The surface member 298 allows the surface profile of the gripping member 216 to be changed quickly and easily without altering the gripping member 216 itself. In some embodiments, for example, the surface member 298 may be screwed and/or clamped to the first surface 232 of the gripping member 216.

It is to be appreciated that the first surface 232 of the gripping member 216 and/or the surface member 298 that may associate with the gripping member 216 may include a surface profile designed and/or chosen to grip the core 228 of the spool 224. For example, the first surface 232 and/or the surface member 298 may be machined, such as by knurling, to create a surface having relatively higher frictional force. In addition, the first surface 232 and/or the surface member 298 may be made of a material that aids in holding the core 228 of the spool 224. For example, the first surface 232 and/or the surface member 298 may be made from plastic or rubber. Alternatively or in addition to the aforementioned, an additive with adhesive properties may be added to the first surface 232 and/or the surface member 298 to create a surface having relatively higher friction.

Similar to the above, the second surface 234 of the gripping member 216 may include a surface profile that operatively associates with the wedge member 230. In some embodiments, the second surface 234 may include an inclined profile, as shown in FIG. 8A. More specifically, the height H of the gripping member adjacent the first end portion 254 may be less than the height H of the gripping member at the second end portion 256. The inclined profile of the second surface 234 may allow the wedge member 230 to slidably engage the second surface 234 and move the gripping member 216 radially outward. It is to be appreciated that the second surface 234 may be designed in view of the surface profile of the wedge member 230 so that the gripping member 216 may move radially inward and/or radially outward from the tubular side wall 208 of the mandrel 202.

Figure 9B:
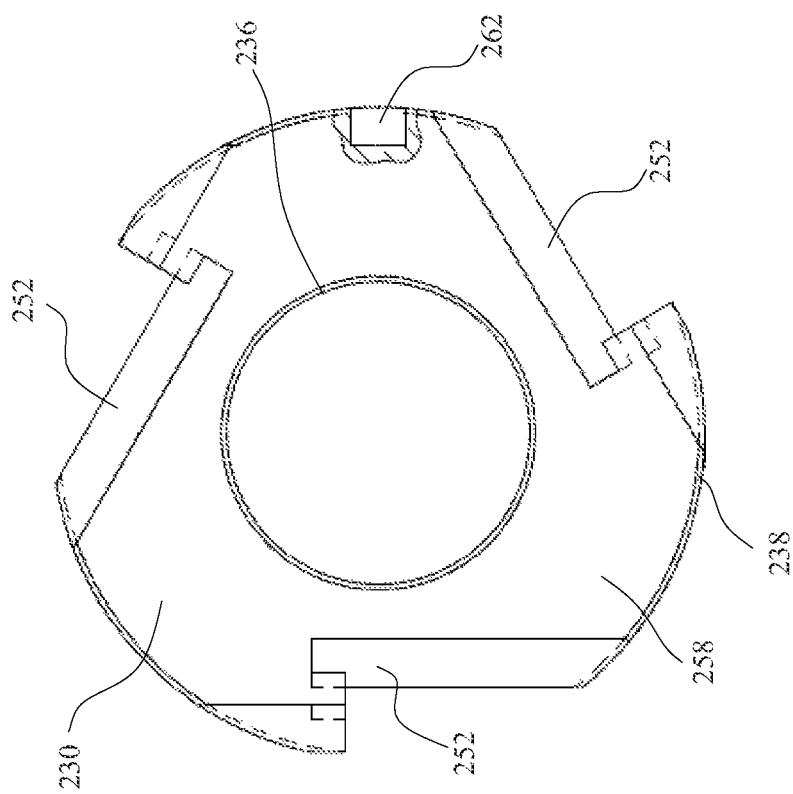
FIG. 9B is an end view of a wedge member in accordance with one non-limiting embodiment of the present disclosure.

The wedge member 230, as illustrated in FIGS. 9A and 9B, may include an internal wedge surface 236. As previously mentioned, the internal wedge surface 236 may be associated with the outer shaft 240. In some embodiments, the internal wedge surface 236 may include one or more threads that may engage one or more threads on the external surface 238 of the outer shaft 240. The internal wedge surface 236 has a circumference sized to operatively engage the outer shaft 240. More specifically, the internal wedge surface 236 is sized such that when the outer shaft 240 rotates, the wedge member 230 is moved longitudinally in at least one of a first direction and a second direction, opposite the first direction. In some embodiments, the internal wedge surface 236 may have a diameter from about 15 mm to about 60 mm and/or from about 20 mm to about 50 mm and/or about 30 mm to about 40 mm, including all 0.1 mm therebetween.

The wedge member 230 may also include an external wedge surface 238, a first end surface 258 and a second end surface 260. The external wedge surface 238 may include one or more engagement portions 252. The engagement portion 252 may include a substantially planar surface having an incline, as shown in FIGS. 9A and 9B. The engagement portion 252 may be configured to interact with the gripping member 216. More specifically, the second surface 234 of the gripping member 216 may slidably associate with the engagement portion 252 of the wedge member 230. In some embodiments, the gripping member 216 may be positioned such that the first end portion 254 of the gripping member 216 is positioned adjacent to the second end surface 260 of the wedge member 230 and the second end portion 256 of the gripping member 216 is positioned adjacent to the first end surface 258 of the wedge member 230. Thus, as the wedge member 230 advances in a first direction, as indicated by arrow A of FIG. 6A, the second end surface 260 of the wedge member 230 moves toward the proximal end portion 242 of the outer shaft and toward the first end portion 254 of the gripping member 216. Similarly, as the wedge member 230 advances in a second direction, as indicated by arrow B of FIG. 6A, the first end surface 260 of the wedge member 230 moves toward the distal end portion 250 of the outer shaft 240 and toward the second end portion 256 of the gripping member 216.

The wedge member 230 may also include a key receiving portion 262, as shown in FIG. 9B. The key receiving portion 262 may be configured to receive a block key 264 or a groove key 272, such as that shown in FIGS. 10A and 10B. The key 264, 272 may slidably engage the inner circumferential surface 212 of the mandrel 202. The key 264, 272 may aid in maintaining alignment of the wedge member 230 during rotation.

Figure 9C:
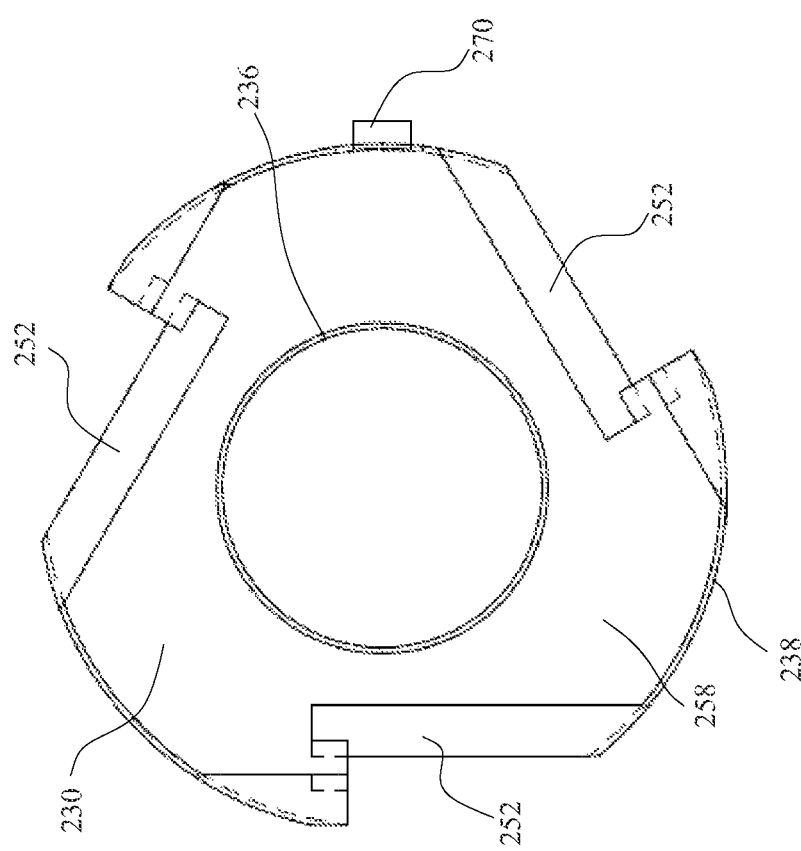
FIG. 9C is an end view of a wedge member in accordance with one non-limiting embodiment of the present disclosure.

In some embodiments, the wedge member 230 may include a protruded key portion 270 that protrudes from the external wedge surface 238, as shown in FIG. 9C. The protruded key portion 270 may be removably connected to the external wedge surface 238 such as by screws, adhesive, or other comparable materials. The protruded key portion 270 may also be machined into the surface of the external wedge surface 238. The protruded key portion 270 may slidably associate with the tubular side wall 208 of the mandrel 202. More specifically, the protruded key portion 270 may slidably engage the groove 266 of the tubular side wall 208. The protruded key portion 270 may aid in alignment of the wedge member 230 as the wedge member 230 moves longitudinally in at least one of a first direction and a second direction. In some embodiments, the protruded key portion 270 may associate with a block key 264 or a groove key 272, such as that shown in FIGS. 10A and 10B. The key 264, 272 may slidably engage the inner circumferential surface 212 of the mandrel 202, and may aid in maintaining alignment of the wedge member 230 during rotation.

It is to be appreciated that commercially available devices may be used to allow the wedge member 230 to be guided along the inner circumferential surface 210 of the mandrel 202. For instance, a linear rail and bearing may be used to guide the wedge member 230 in a longitudinal direction along the inner circumferential surface 210 of the mandrel 202. Exemplary linear rails and bearings are manufactured by NKS Corporation of Ann Arbor, Mich., or Thomson Industries, Inc. of Radford, Va.

Referring to FIGS. 11A and 11B, the outer shaft 240 may include a proximal end portion 248 and a distal end portion 250, opposite the proximal end portion 248. The proximal end portion 248 of the outer shaft 240 may be configured to connect to the clamp member 217. The clamp member 217 may be connected to the outer shaft 240 such that as the handle member 218 rotates the outer shaft may rotate. It is to be appreciated that the clamp member 218 may be connected to a portion of the proximal end portion 248 of the outer shaft 240 by any means that allows rotational movement to be translated from the handle member 218 to the outer shaft 240. For example, the clamp member 217 may be connected to the outer shaft 240 mechanically such as with screws or clamps. Further, the clamp member 217 may be connected to the outer shaft 240 chemically such as with adhesives.

The outer shaft 240 may include an external surface 242 and an internal surface 244. As previously mentioned, a portion of the external surface 242 may include one or more threads (not shown). The one or more threads may associate with the one or more threads present on the internal wedge surface 236. The one or more threads on the external surface 242 may allow the outer shaft 240 to engage and move the wedge member 230 in at least one of a first direction and a second direction. The outer shaft 240 may also include an internal surface 244. The internal surface 244 includes an internal circumferential surface configured to receive an inner shaft 302, as illustrated in FIG. 6A. The internal surface 244 of the outer shaft 240 may be a substantially smooth surface such that the inner shaft 302 may be slidably engaged with the internal surface 244 of the outer shaft 240.

Figure 12:
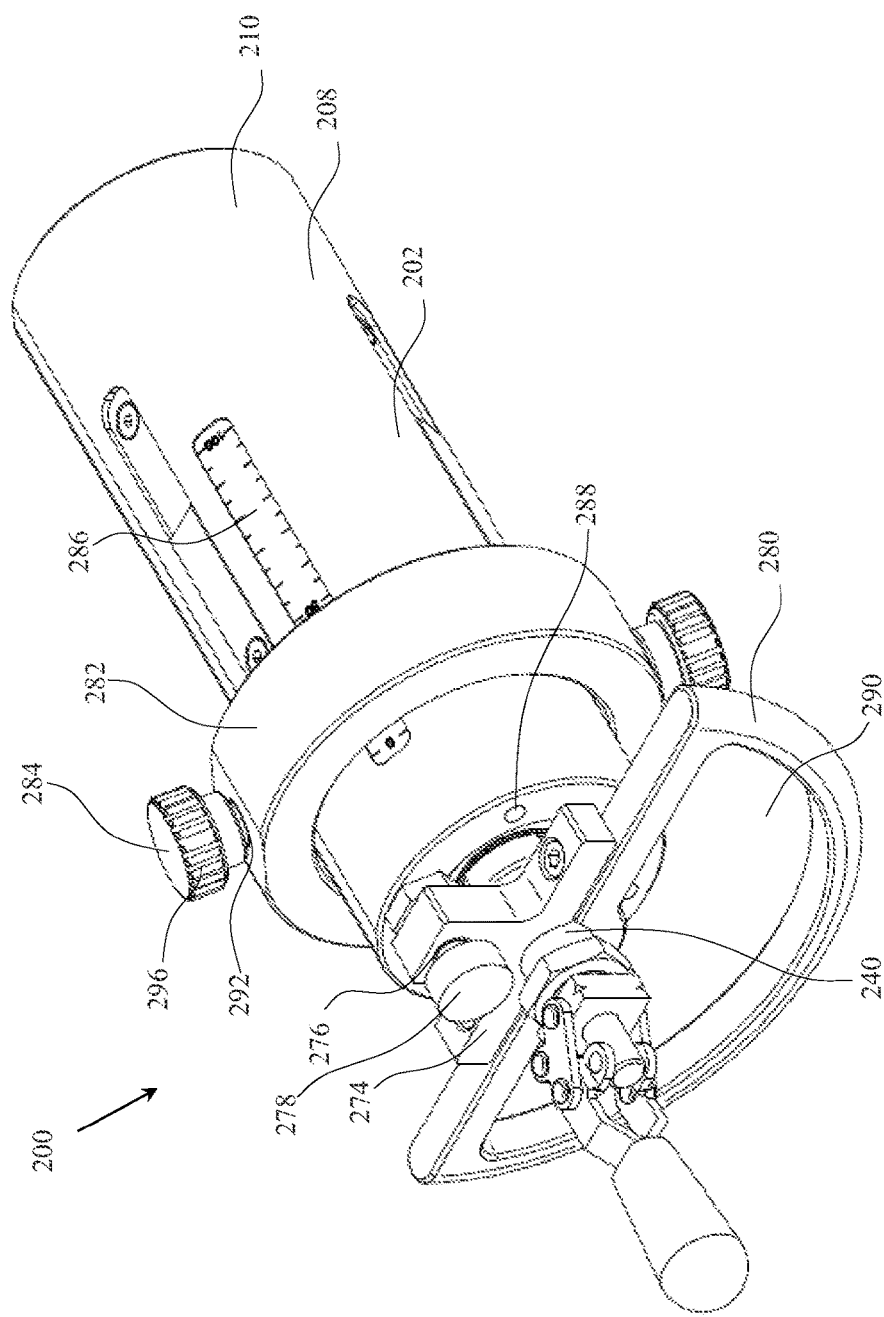
FIG. 12 is a perspective view of a loading apparatus in accordance with one non-limiting embodiment of the present disclosure.

In some embodiments, the loading apparatus 200 may also include at least one of a stabilizing plate member 274, a holding member 280, a ring member 282, and ruler 286, as illustrated in FIG. 12. The stabilizing member 274 may be connected to the proximal end portion of the outer shaft 240. More specifically, the stabilizing member 274 may surround a portion of the external surface 242 of the outer shaft 240. The stabilizing member 274 may define a stabilizing aperture 276 configured to receive a stabilizing pin 278. The stabilizing pin 278 is configured to extend through the stabilizing aperture 276. Further, a portion of the stabilizing pin 278 is also configured to extend into a stabilizing slot 288 defined by the mandrel 202, also shown in FIG. 6A. The stabilizing pin 278 extending through the stabilizing aperture 276 and into the stabilizing slot 288, aids in preventing the mandrel 202 from rotating relative to the outer shaft 240.

The loading apparatus 200 may also include a holding member 280 positioned adjacent the stabilizing plate member 274 and the outer shaft 240. The holding member 280 may surround a portion of the outer shaft 240. Further, the holding member 280 may be connected to the stabilizing pate member 274. More specifically, the holder member 280 may be connected to the stabilizing plate member 274 with screws, clamps, or pins, for example. The holding member 280 may define a holding aperture 290. The holding aperture 290 may be sized so that an operator is able to rest at least a portion of his or her hand within the holding aperture 290. Thus, an operator may use the holding member 280 to grip and hold the loading apparatus 200.

Further, in some exemplary embodiments, the holding member 280 may be attached to the outer shaft 240. Thus, the holding member 280 may be used to rotate the outer shaft 240 about the central longitudinal axis, which may cause the wedge member 230 to move in a longitudinal direction along the inner circumferential surface 212 of the mandrel 202. As previously described, the movement of the wedge member 230 may result in the gripping member 216 extending radially outward from or descending radially inward through the tubular side wall 208 of the mandrel 202, as shown in FIG. 6A. It is to be appreciated that the holding member 280 may be a shape that allows the operator to seize and rotate the holding member 280 about the central longitudinal axis 246.

As previously described, the holding member 280 may be attached to the stabilizing plate 274 and the outer shaft 240. Thus, when the stabilizing pin 278 is disengaged from the stabilizing slot 288, the holding member 280 and the outer shaft 240 may rotate about the central longitudinal axis 246, as shown in FIG. 6A. Likewise, when the stabilizing pin 278 is engaged with the stabilizing slot 288, the holding member 280 and the outer shaft 240 may be prevented from rotating about the central longitudinal axis 246.

The loading apparatus 200 may also include a ring member 282. The ring member 282 may substantially surround the tubular side wall 208 of the mandrel 202. The ring member 282 may slidably associate with the tubular side wall 208. Thus, the ring member 282 may slid along the length of outer circumferential surface 210 the tubular side wall 208. The ring member 282 may define a tightening aperture 292. The tightening aperture 292 may be configured to receive a tightening member 284. In some embodiments, the tightening aperture 292 may include one or more threads. Similarly, the tightening member 284 may include one of more threads. The threads of the tightening aperture 292 may engage the threads of the tightening member 284 such that the tightening member 284 may be screwed into a position. The tightening member 284 may include a proximal end portion 296 and a distal end portion (not shown). The tightening member 284 may be rotated such that the distal end portion engages the tubular side wall 208 of the mandrel 202. More specifically, the tightening member 284 may be rotated such that the distal end portion applies pressure to the outer circumferential surface 210 of the tubular side wall 208. The pressure exerted on the tubular side wall 208 may prevent the ring member 282 from moving in a longitudinal direction along the outer circumferential surface 210 of the tubular side wall 208 or from rotating about the outer circumferential surface 210 of the tubular side wall 208. Further to the above, the ring member 282 may provide a surface against which the spool 244 may abut. Thus, the ring member 282 may support a portion of the spool 244 during movement of the spool.

The loading apparatus 200 may also include a measurement indicator 286. The measurement indicator 286 may be disposed on the outer circumferential surface 210 of the tubular side wall 208. The measurement indicator 286 may be used by an operator to ensure placement of the spool in a given location on the mandrel 202. In some embodiments, the measurement indicator 286 may be used in cooperation with the ring member 282. More specifically, the ring member 282 may be positioned on the tubular side wall 208 at a certain location as indicated by the measurement indicator 286. Thus, when the spool is loaded onto the mandrel 202, the operator merely needs to position the spool against the ring member 282 to place the spool in its desired position.

Figure 13:
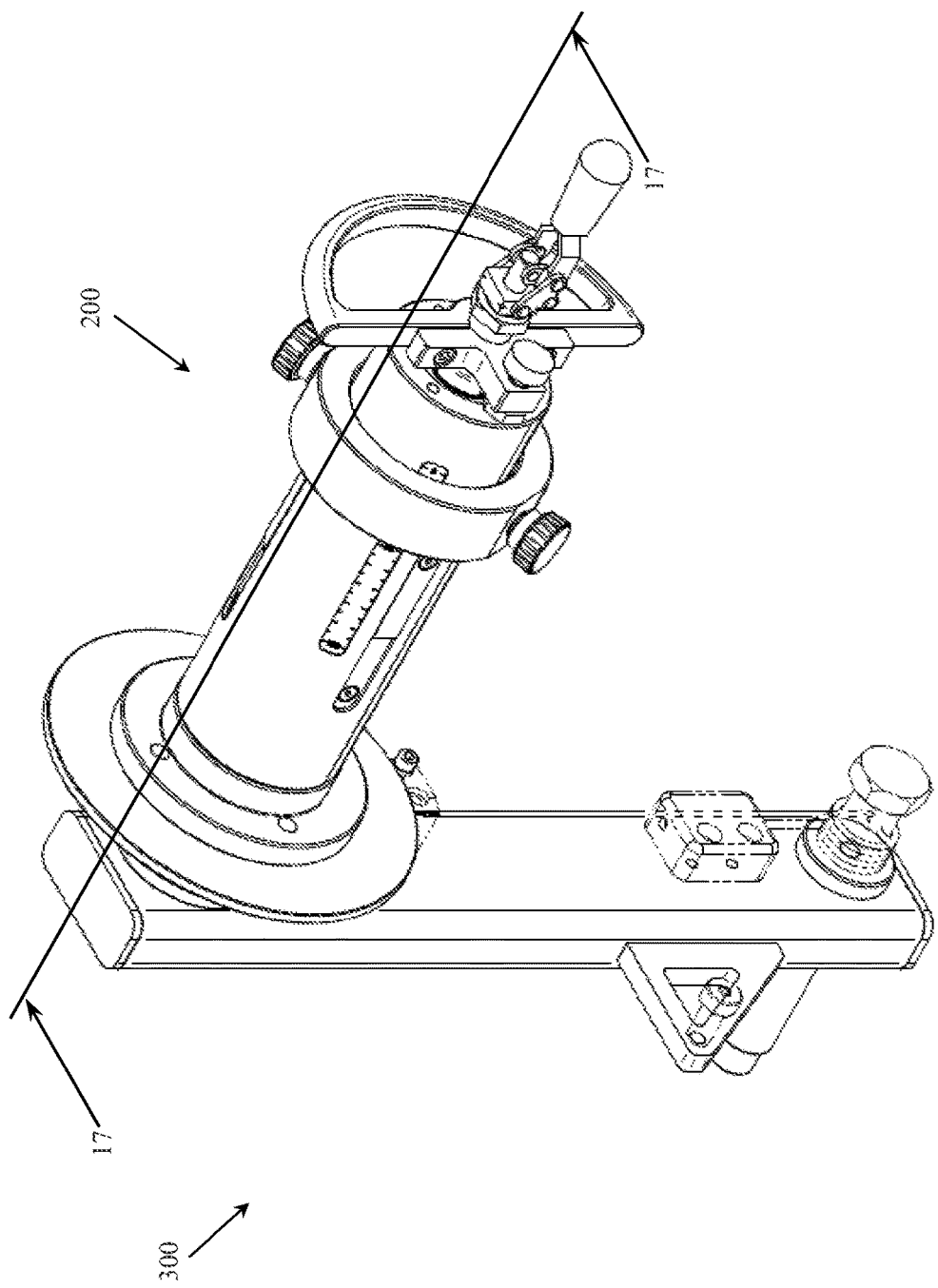
FIG. 13 is a perspective view of a loading apparatus and an unwind apparatus in accordance with one non-limiting embodiment of the present disclosure.
Figure 14:
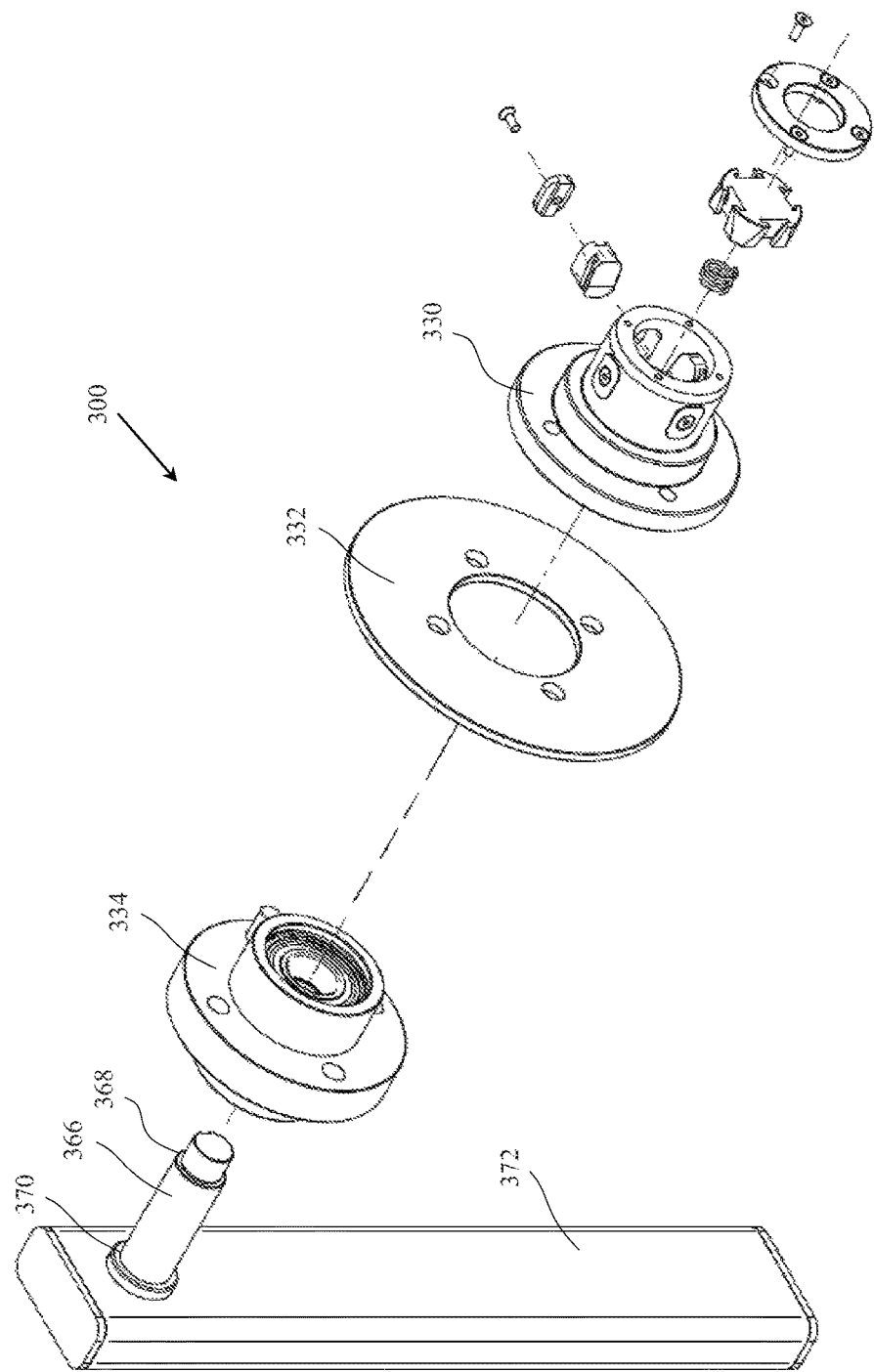
FIG. 14 is an exploded view of an unwind apparatus in accordance with one non-limiting embodiment of the present disclosure.

As previously mentioned, the loading apparatus 200 may be configured to engage with an unwind apparatus 300, as illustrated in FIGS. 13 and 14. As discussed in more detail below, the unwind apparatus and the loading apparatus may be reconfigurable. For example, in a first configuration, the loading apparatus may be connected with the unwind apparatus. In a second configuration, the loading apparatus may be disconnected from the unwind apparatus.

Generally, the loading apparatus 200 includes one or more structural members that allow it to connect to the unwind apparatus 300. As previously mentioned, the loading apparatus may include a clamp member 217 that may include a handle member 218, as shown in FIG. 6A. The handle member 218 may rotate about a central handle axis 220. The handle member 218 may be used to translate rotational movement to the outer shaft 240. In addition, the handle member 218 may pivot about a pivot point 222, such that the handle member 218 may be positioned at some angle to and/or substantially perpendicular to the central handle axis 220.

Figure 17:
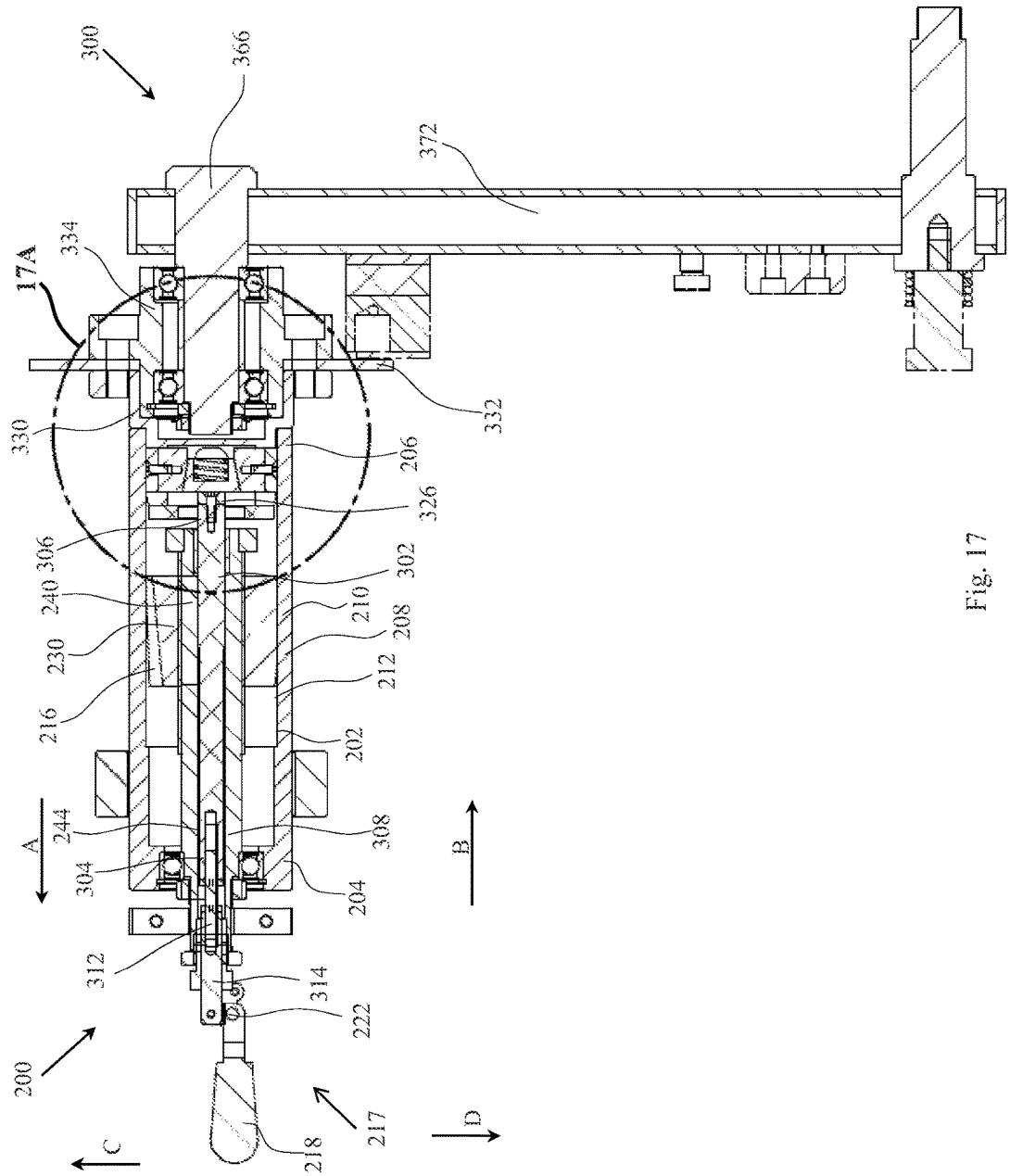
FIG. 17 is a cross-sectional view of the loading apparatus connected to the unwind apparatus of FIG. 13 taken along line 17-17 in accordance with one non-limiting embodiment of the present disclosure.

The clamp member 217 may also include a plunger 314, which may be adjacent to the handle member 218. The plunger 314 may be slidably engaged with the handle member 218. Thus, as the handle member 218 is rotated at an angle to the central handle axis 220, the plunger 314 may move in a first direction, as indicated by arrow A, toward to the handle member 218, as shown in FIG. 17. Likewise, when the handle member 218 is rotated from some angle to the central handle axis 220 to a position where the handle member 218 is substantially parallel to the central handle axis 220, the plunger 314 may move in a second direction, as indicated by arrow B, away from the handle member 218, as shown in FIG. 17.

It is to be appreciated that the handle member 218 may be configured to move the plunger 314 in the opposite manner. For example, when the handle member 218 is rotated at an angle to the central handle axis 220, the plunger may move in a direction indicated by arrow B. Similarly, when the handle member 218 is rotated such that the handle member 218 is substantially parallel to the central handle axis 220, the plunger may move in a direction as indicated by arrow A.

The plunger 314 may include a proximal end portion 316 and a distal end portion 318, opposite the proximal end portion 316. The proximal end portion 316 of the plunger 314 may be adjacent to the handle member 218. The distal end portion 318 of the plunger 314 may be adjacent to the proximal end portion 248 of the outer shaft 240. The distal end portion 318 of the plunger 314 may define a rod slot 320. The rod slot 320 may be configured to receive a rod member 312. The rod member 312 may include a first end portion 322 and a second end portion 324, opposite the first end portion 322. The first end portion 322 of the rod member 312 may be received within the rod slot 320. The first end portion 322 of the rod member 312 may be adjustable with respect to the rod slot 320. For example, the rod member 312 may be adjusted so that the first end portion 322 of the rod member 312 substantially fills the rod slot 320. Alternatively, the rod member 312 may be placed within the rod slot 320 such that the first end portion 322 of the rod member 312 only fills a portion of the rod slot 320. Thus, another portion of the rod slot 320 remains unfilled by the rod member 312. The second end portion 324 of the rod member 321 may remain external to the plunger 314. The rod member 312 may be associated with the rod slot 320 such that when the plunger 314 moves, the rod member 312 moves in a similar direction. For example, when the plunger 314 moves in a first direction, as indicated by arrow A, toward the handle member 218, the rod member 312 may also move in the first direction toward the handle member 218.

As illustrated in FIG. 6A, the loading apparatus 200 may include an inner shaft 302 having a proximal end portion 304 and a distal end portion 306, opposite the proximal end portion 304. The inner shaft 302 may also include an outer circumferential surface 308 that may slidably associate with the internal surface 244 of the outer shaft 240. Further, the proximal end portion 204 of the inner shaft 302 may define a rod slot 310 configured to receive the second end portion 324 of the rod member 312. The rod slot 310 may substantially surround at least a portion of the second end portion 324 of the rod member 312. More specifically, the second end portion 324 of the rod member 312 may be adjusted with respect to the rod slot 310. For example, in some embodiments, the second end portion 324 of the rod member 312 may substantially fill the rod slot 310. In some other embodiments, the second end portion 324 of the rod member 312 may fill only a portion of the rod slot 310 such that a portion of the rod slot 310 remains unfilled by the second end portion 324 of the rod member 312.

The rod member 312 may operatively link the plunger 314 with the inner shaft 302. More specifically, the rod member 312 may be operatively engaged with both the plunger 314 and the inner shaft 302 such that when an operator pivots the handle member 218, the plunger 314 may move in a first direction, as indicated by arrow A, toward the handle member 218. The movement of the plunger 314 in the first direction may also result in the rod member 312 moving in the first direction toward the handle member 218. Similarly, the second end portion 324 may engage the inner shaft 302 such that the inner shaft 302 moves with the plunger 314 and the rod member 312 in the first direction toward the handle member 312. Thus, the outer circumferential surface 308 of the inner shaft 302 may move longitudinally along the internal surface 244 of the outer shaft 240 in the first direction. It is to be appreciated that the rod member may be any rigid member that may be used to transfer the motion of the plunger 314 to that of the inner shaft 302. The rod member 312 may be configured to be adjusted within the rod slots 310, 320 to adjust the length between the plunger 314 and the inner shaft 302. Thus, the rod member 312 may allow the distance between the plunger 314 and the inner shaft 302 to be increased and/or decreased.

Likewise, the rod member 312 may be operatively engaged with both the plunger 314 and the inner shaft 302 such that when an operator pivots the handle member 218, such that the handle member 218 may be substantially parallel with the central handle axis 220, the plunger 314 may move in a second direction, as indicated by arrow B, away from the handle member 218. The movement of the plunger 314 in the second direction may also result in the rod member 312 moving in the second direction away from the handle member 218. Similarly, the second end portion 324 may engage the inner shaft 302 such that the inner shaft 302 moves with the plunger 314 and the rod member 312 in the second direction away from the handle member 312. Thus, the outer circumferential surface 308 of the inner shaft 302 may move longitudinally along the internal surface 244 of the outer shaft 240 in the second direction.

As previously mentioned, an inner shaft 302 may include a proximal end portion 304 and a distal end portion 306, opposite the proximal end portion 304. In some embodiments, a bumper member 326 may be adjacent to the distal end portion 306 of the inner shaft 302. More specifically, the bumper member 326 may be connected with the distal end portion 306 of the inner shaft 302. The bumper member 326 may be connected mechanically or chemically, for example. Mechanical connections may include screws, clamps, and/or pins. Chemical connections may include adhesives. The bumper member 326 may move in the same direction as the inner shaft 302. Thus, when the inner shaft 302 moves in a first direction, as indicated by arrow A, the bumper member 326 may also move in the first direction, and vice versa. The bumper member 326 may be configured to engage and disengage the unwind apparatus 300.

The unwind apparatus 300, as shown in FIGS. 13 and 14 may be connected to the loading apparatus 200. Generally, loading apparatus 200 may connect to a portion of the unwind apparatus 300. Further, the loading apparatus 200 may rotate with a portion of the unwind apparatus 300. The unwind apparatus 300 includes a hub assembly 334 adjacent to the first side of a brake member 332 and a mount member 330 adjacent to a second side of the brake member 332. The hub assembly 334 may be configured to allow the loading apparatus 200 to rotate and/or for the material 226 to be unwound from the core 228 of the spool 224. The mount member 330 may be configured to engage the loading apparatus 200. In addition, the brake member 332 may be configured to control the unwind of the spool 224 and/or the rotation of the loading apparatus 200. The unwind apparatus 300 may also include an unwind arm 366 having a proximal end portion 368 and a distal end portion 370, opposite the proximal end portion 368. The distal end portion 370 may be connected to a support member 372 and the proximal end portion 368 may be configured to receive at least one of the hub assembly 334, the brake member 332, and the mount member 330. The support member 372 may be a substantially fixed, rigid member that is adapted to support the loading apparatus and the spool.

Figure 15B:
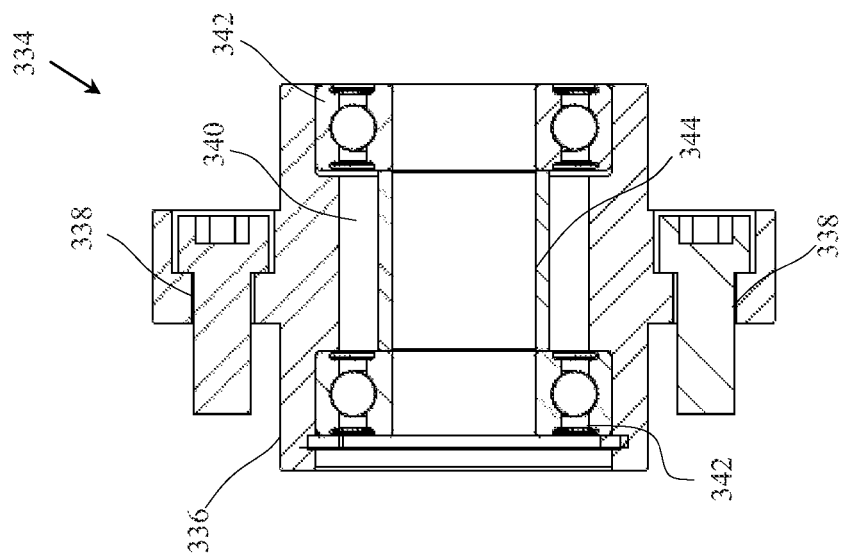
FIG. 15B is a cross-sectional view of the hub assembly of FIG. 15A taken along line 15B-15B in accordance with one non-limiting embodiment of the present disclosure.
Figure 15A:
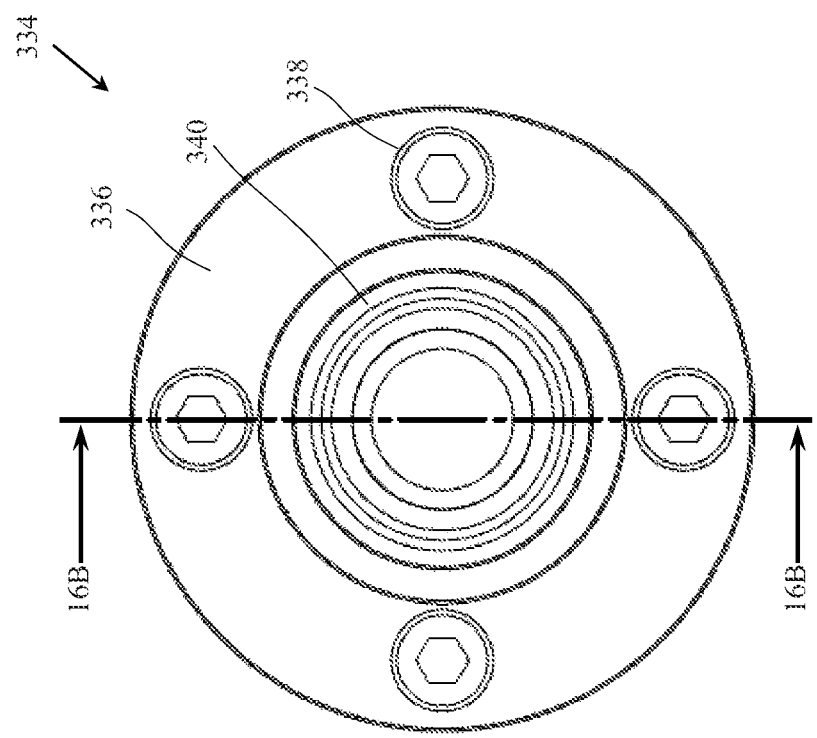
FIG. 15A is an end view of a hub assembly in accordance with one non-limiting embodiment of the present disclosure.

Referring to FIGS. 15A and 15B, the hub assembly 334 may be configured to allow the loading apparatus 200 and/or the spool 224 to rotate. The hub assembly 334 includes a housing 336, which may define an opening 338 configured to receive a screw or a pin or other similar device used to secure the position of the housing. The housing 336 may also define a housing aperture 340. The housing aperture 340 may be configured to receive a bearing 342. In some embodiments, the housing aperture 340 may be configured to receive at least two bearings 342. The at least two bearings 342 may be separated by a spacer 344. The bearing 342 allows the housing 336 to rotate. The housing 336 may be connected to the brake member 332, as shown in FIG. 14.

Figure 16:
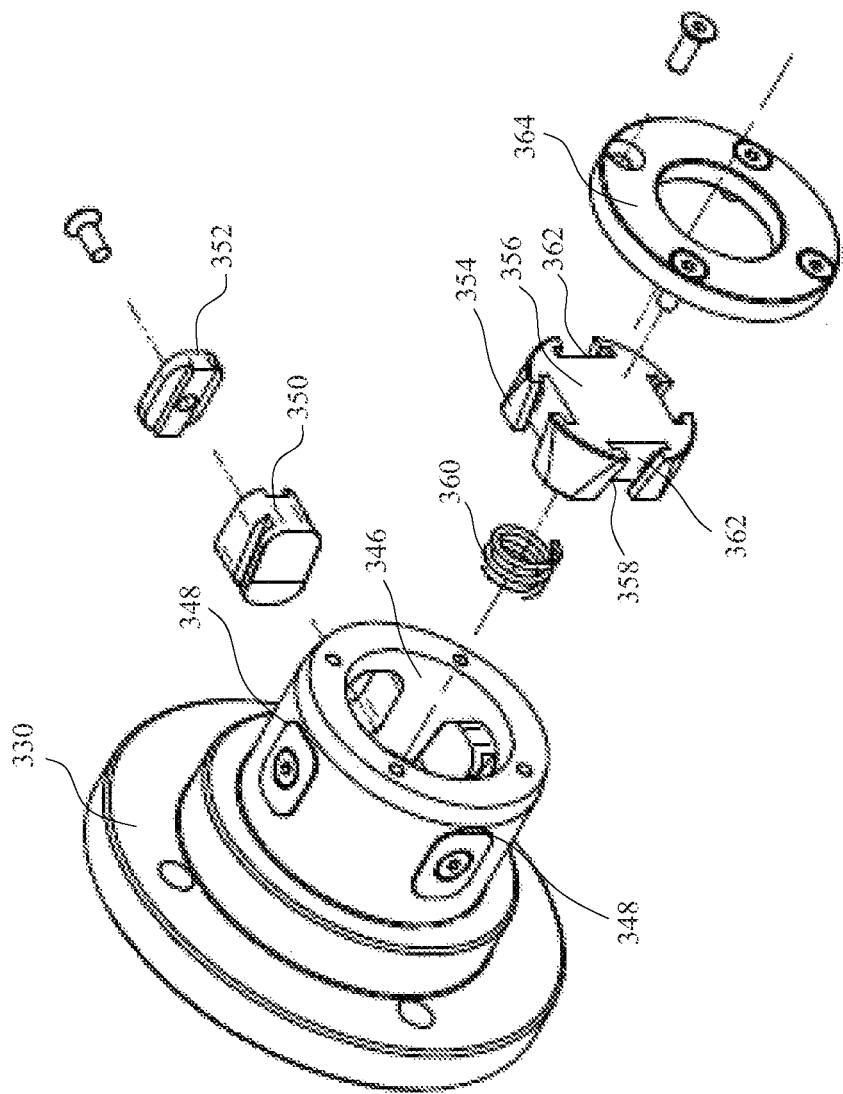
FIG. 16 is an exploded view of a mount member in accordance with one non-limiting embodiment of the present disclosure.

The opposite side of the brake member 332 may be connected to the mount member 330, as shown in FIG. 14. The mount member 330 may engage the loading apparatus 200. More specifically, as shown in FIG. 16, the mount member 330 may include an internal cavity 346 and an aperture 348. The aperture 348 may be adapted to receive a bracing member 350. The bracing member 350 may move telescopically through the aperture 348. Stated another way, the bracing member 350 may extend radially outward through the aperture 348 and/or descend radially inward through the aperture 348. A surface plate 352 may be connected to a portion of the bracing member 350. The surface plate 352 may be used to change the topography of the bracing member 350. For example, if a textured surface was preferred to engage the mandrel 202, a surface plate 352 having a textured surface may be connected to the bracing member 350. Thus, when the bracing member 350 extends radially outward to engage the mandrel 202, the textured surface of the surface plate 352 will interact with the inner circumferential surface 212 of the mandrel 202.

To move the bracing member 350 radially inward and/or radially outward, the bracing member 350 may associate with a block member 354. The block member 354 may be positioned within the internal cavity 346. The block member 354 may include a first surface 356 and a second surface 358. The first surface 356 of the block member 354 may be configured to engage the distal end portion 306 of the inner shaft 302 and/or the bumper member 326, which will be explained in more detail herein. The second surface 358 of the block member 354 may be associated with a tension member 360, such as a spring. The tension member 360 engages the second surface 358 of the block member 354 such that the block member 354 may be pushed in a direction opposite the tension member 360 and/or toward the distal end portion 306 of the inner shaft 302. The movement of the block member 358 may allow the bracing member 350 to move radially inward and/or radially outward with respect to the aperture 348. More specifically, the block member 354 may include a notched portion 362. The notched portion 362 may include an inclined surface. More specifically, the notched portion 362 may be inclined such that when the tension member 360 pushes against the block member 354 and the block member 354 is not under pressure from the inner shaft 302, the bracing member 350 may not extend radially outward through the aperture 348. Similarly, when the inner shaft 302 exerts pressure on the block member 354 to overcome the pressure exerted by the tension member 360, and the block member 354 moves toward the tension member 360, the inclined notched portion 362 may cause the bracing member 350 to move radially outward through the aperture 348.

Still referring to FIG. 16, in some embodiments, a block plate 364 may be connected to a portion of the mount member 330. The block plate 364 may be connected to a portion of the mount member 330 such that it is positioned adjacent to the second surface 358 of the block member 354. Thus, when the block member 354 undergoes pressure from the tension member 360 and is pushed in a direction opposite the tension member 360, the block plate 364 may associate with the first surface 356 of the block member 354 resisting additional movement of the block member 354. Stated another way, the block plate 364 may prevent the block member 354 from exiting the internal cavity 346 of the mount member 330.

Figure 17A:
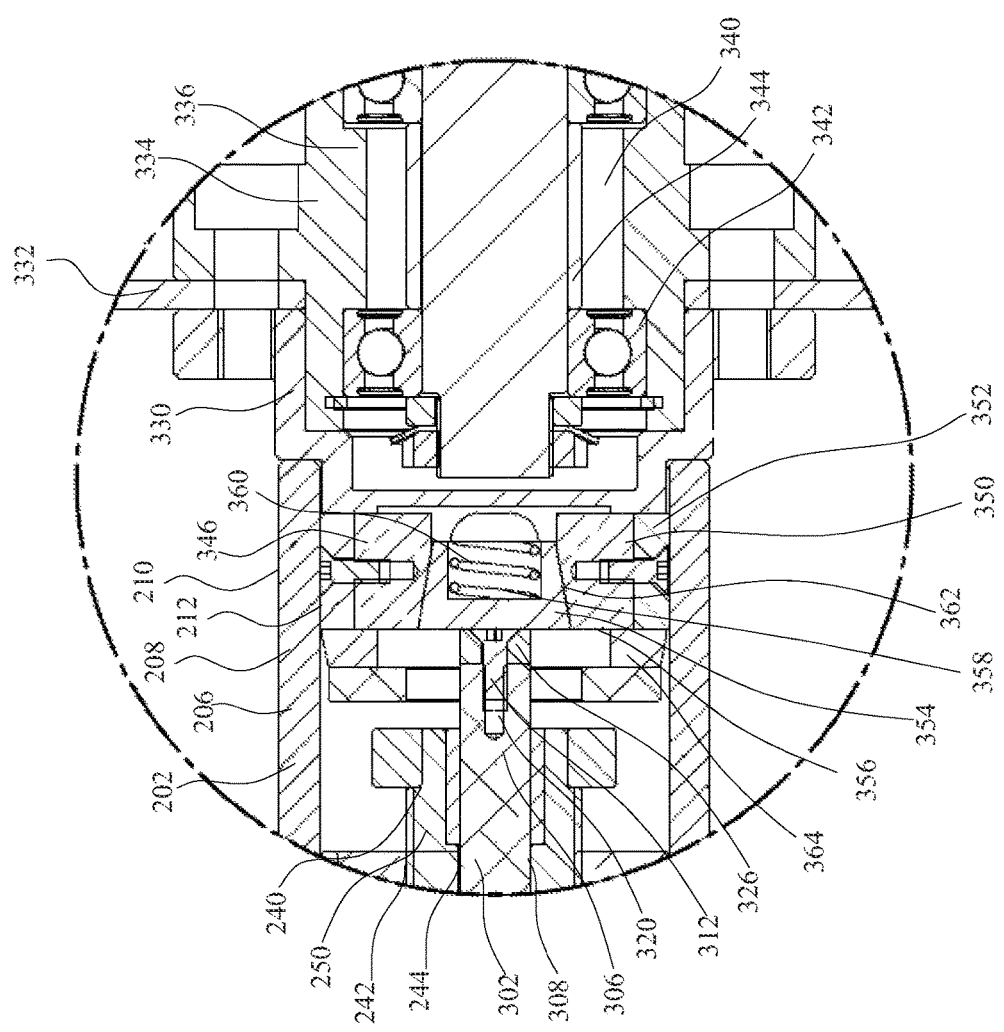
FIG. 17A is a detailed view of a portion of the loading apparatus connected to the unwind apparatus of FIG. 17 in accordance with one non-limiting embodiment of the present disclosure.
Figure 18:
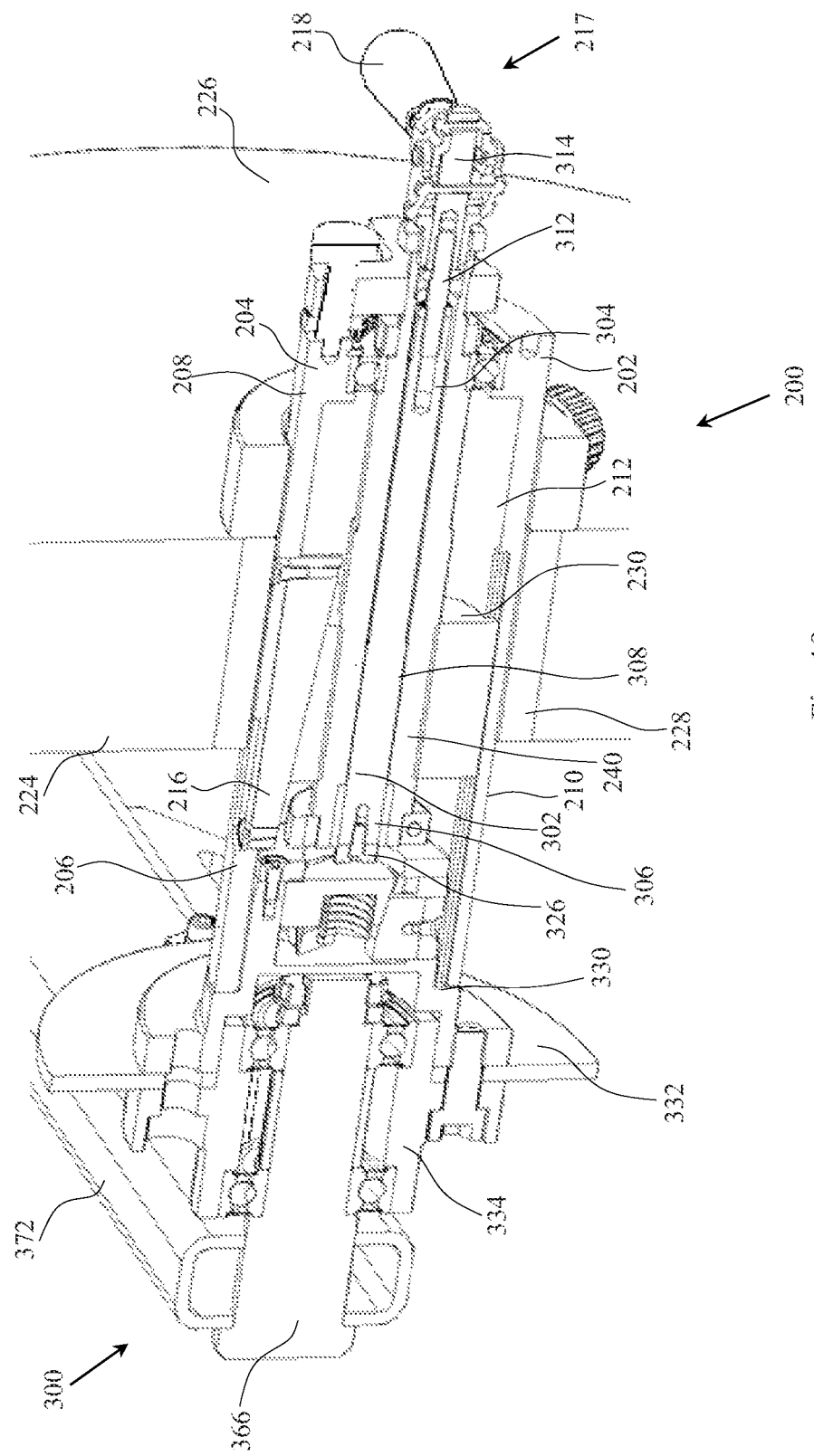
FIG. 18 is a partial, schematic representation of the loading apparatus connected to the unwind apparatus in accordance with one non-limiting embodiment of the present disclosure.

As illustrated in FIGS. 17, 17A, and 18, the loading apparatus 200 may be connected to the unwind apparatus 300. More specifically, a portion of the inner circumferential surface 212 of the mandrel 202 may substantially surround a portion of the mount member 330. Once the mandrel 202 has been positioned on a portion of the mount member 330, the handle member 218 may be pivoted about the pivot point 222. The pivoting motion of the handle member 218 may allow the plunger 314 to move in a second direction, as indicated by arrow B, which may be in a direction toward the unwind apparatus 300. The plunger 314 may be configured to engage and move the rod member 312 in the second direction. The rod member 312 may then engage the inner shaft 302 such that the inner shaft 302 moves in the second direction, as indicated by arrow B. The outer circumferential surface 308 of the inner shaft 302 slidably engages the internal surface 244 of the outer shaft 240. The distal end portion 306 of the inner shaft 302 may engage the block member 354 disposed within the internal cavity 346 of the mount member 330. More specifically, the distal end portion 306 of the inner shaft 302 may engage the first surface 356 of the block member 354 causing the block member 354 to move in the second direction. The second surface 358 of the block member 354 engages the tension member 360 and may compress the tension member 360. Further, as the block member 354 moves in the second direction, the notched portion 362 may slidably engage a bracing member 350. As the block member 354 progresses in the second direction, the bracing member 350 may extend radially outward, as indicated by arrow C, through the aperture 348, as shown in FIG. 16, and engage the inner circumferential surface 212 of the mandrel 202. The bracing member 350 supports the loading apparatus 200 during unwind of the spool 224, as shown in FIG. 18. Once the bracing member 350 has engaged the mandrel 202 and the loading apparatus 200 is supported, the hub assembly 334 may allow the loading apparatus 200 to rotate and/or the spool 224 to be unwound.

Once a spool 224 has been depleted of material 226 and only the core 228 of the spool remains, the loading apparatus 200 may be disengaged from the unwind apparatus 300 so that another spool may be loaded and unwound. To disengage the loading apparatus 200, the handle member 218 may be pivoted about the pivot point 222. The pivoting motion of the handle member 218 may allow the plunger 314 to move in a first direction, as indicated by arrow A, which may be in a direction away from the unwind apparatus 300. The plunger 314 may be configured to engage and move the rod member 312 in the first direction. The rod member 312 may then engage the inner shaft 302 such that the inner shaft 302 moves in the first direction. The outer circumferential surface 308 of the inner shaft 302 slidably engages the internal surface 244 of the outer shaft 240. The distal end portion 306 of the inner shaft 302 may disengage the block member 354 disposed within the internal cavity 346 of the mount member 330. More specifically, the distal end portion 306 of the inner shaft 302 may disengage the first surface 356 of the block member 354 causing the block member 354 to move in the first direction, due to the force exerted on the block member 254 by the tension member 360. The tension member 360 engages the second surface 358 of the block member 354 causing the block member 254 to move in the first direction and allowing the tension member 360 to extend. Further, as the block member 354 moves in the first direction, the notched portion 362 may slidably engage the bracing member 350. As the block member 354 progresses in the first direction, as indicated by arrow A, the bracing member 350 may descend radially inward, as indicated by arrow D, through the aperture 348 and may disengage the inner circumferential surface 212 of the mandrel 202. Stated another way, the bracing member 350 may release the mandrel 202. Once the bracing member 350 has disengaged the mandrel 202, the loading apparatus 200 may be removed from the portion of the mount member 330.

In view of the aforementioned, a method for loading a spool of material on an unwinding apparatus may include the following steps. A mandrel 202 may be provided. The mandrel 202 may include a tubular side wall 208 that extends longitudinally between a first end portion 204 and a second end portion 206. The tubular side wall 208 may include an outer circumferential surface 210 and an inner circumferential surface 212. A gripping member 216 may be retracted radially inward through an aperture 214 in the tubular side wall 208 of the mandrel 202. The gripping member 216 may be retracted by moving a wedge member 230 in a second direction, as indicated by arrow B of FIG. 17, longitudinally along the inner circumferential surface 212 of the tubular side wall 208 of the mandrel 202. A spool 224 may be provided. The spool 224 may include a core 228 and a web material 226 wound around the core 228. The mandrel 202 may be inserted into the core 228 of the spool 224. The gripping member 216 may be projected radially outward through the aperture 214 in the tubular side wall 208 of the mandrel 202. The gripping member 216 may be projected outward to grip the core 228. The gripping member 216 may be projected outward by moving a wedge member 230 in a first direction, as indicated by arrow A of FIG. 17, longitudinally along the inner circumferential surface 212 of the tubular side wall 208. Generally, the second direction may be opposite the first direction. The core 228 may be released by moving the wedge member 230 longitudinally along the inner circumferential surface 212 of the tubular side wall 208 in the second direction.

Further to the above, the mandrel 202 may be adjacent to a clamp member 217. The clamp member 217 may include a handle member 218. The handle member 218 may be rotated to at least one of retract and project the gripping member 216.

Further still, the mandrel 202 may be connected to a mount member 330. The mount member 330 may include an internal cavity 346 that houses a bracing member 350, a block member 354, and a tension member 360. An inner shaft 304 may engage the block member 354 moving the block member in a second direction, as shown in FIG. 17 by arrow B. The block member 354 may engage the bracing member 350. The bracing member 350 may be projected radially outward to engage the core 228 of the spool 224. The hub assembly 334 may rotate the loading apparatus and/or the spool. Once the material of the spool 224 has been unwound and the core 228 of the spool is empty, the mandrel 202 may be removed from the mount member 330. The bracing member 350 may be retracted radially inward, which releases the mandrel 202.

It is to be appreciated that the movement of the gripping member 216 may be controlled by other means. More specifically, a portion of the gripping member 216 may associate with an expandable member, such as an inflatable balloon. The expandable member may be substantially surrounded by the outer circumferential surface of the mandrel 202. The expandable member may be operatively connected to a fluid source. The fluid source may supply air and/or liquid to the balloon member to inflate the balloon member such that it extends toward the inner circumferential surface 212 of the mandrel 202 and engages the second surface 234 of the gripping member 216, which may cause the gripping member 216 to protrude through the aperture 214 in the tubular side wall 208 of the mandrel 202. Likewise, the expandable member may be operatively connected to a vacuum source. The vacuum source may be used to remove the fluid from the expandable member such that the expandable member deflates. As the expandable member deflates, at least a portion of the expandable member may descend from the inner circumferential surface 212 of the mandrel 202 and the gripping member 216 may move radially inward through the aperture 214 in the tubular side wall 208 of the mandrel 202.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A loading apparatus for supporting a spool comprising a core and a web of material wound around the core, the apparatus comprising:
 a mandrel adapted to be received by the core, the mandrel comprising a tubular side wall extending longitudinally between a first end portion and a second end portion, the tubular side wall including an outer circumferential surface and an inner circumferential surface, wherein the inner circumferential surface of the mandrel includes a groove configured to slidably engage at least one of a block key and a groove key
 an aperture in the tubular side wall;
 a gripping member telescopically received within the aperture, the gripping member including a first surface and a second surface, the first surface facing radially outward from the tubular side wall;
 a wedge member slidably associated with the second surface of the gripping member, the wedge member received within the mandrel and adapted to move longitudinally along the inner circumferential surface of the tubular side wall;
 wherein as the wedge member moves longitudinally in a first direction, the first surface of the gripping member moves radially outward to press against the core; and
 wherein as the wedge member moves longitudinally in a second direction opposite the first direction, the first surface of the gripping member moves radially inward to release the core.

2. The loading apparatus of claim 1, further comprising an outer shaft having an internal outer shaft surface and an external outer shaft surface, wherein the wedge is movably associated with the external outer shaft surface.

3. The loading apparatus of claim 2, further comprising an inner shaft having a proximal end portion and a distal end portion opposite the proximal end portion, wherein at least a portion of the inner shaft is substantially surrounded by the outer shaft, and wherein the inner shaft is slidably associated with the outer shaft.

4. The loading apparatus of claim 3, further comprising a rod having a proximal end portion and a distal end portion opposite the proximal end portion, wherein the distal end portion of the rod is operatively engaged with the proximal end portion of the inner shaft.

5. The loading apparatus of claim 4, further comprising a clamp member comprising a plunger and a handle, wherein the plunger includes a distal end potion and a proximal end portion opposite the distal end portion, and wherein the handle is adjacent to the proximal end portion of the plunger and the rod is adjacent to the distal end portion of the plunger.

6. The loading apparatus of claim 5, wherein the handle is configured to rotate the outer shaft.

7. The loading apparatus of claim 3, further comprising a bumper member adjacent the distal end portion of the inner shaft.

8. The loading apparatus of claim 2, wherein the external outer shaft surface includes threads and an internal wedge surface of the wedge includes threads, and wherein the threads of the outer shaft operatively engage the threads of the internal wedge surface.

9. The loading apparatus of claim 2, further comprising a stabilizing plate member adjacent the external shaft surface of the outer shaft, wherein the stabilizing plate defines a stabilizing aperture, wherein the stabilizing aperture is configured to receive a stabilizing pin.

10. The loading apparatus of claim 1, further comprising a surface member removably connected to the gripping member.

11. The loading apparatus of claim 1, further comprising at least one of a block key and a groove key connected to at least the key receiving portion and the protruded key portion of the wedge, wherein the at least one of the block key and the groove key slidably engages the inner circumferential surface of the mandrel.

12. The loading apparatus of claim 1, further comprising a holding member adjacent the mandrel.

13. The mandrel support apparatus of claim 1, further comprising a ring member disposed about the outer circumferential surface of the mandrel, wherein the ring is configured to abut a spool.

14. A loading apparatus comprising:
 a clamp member;
 an inner shaft having a proximal end portion and a distal end portion opposite the proximal end portion, wherein the clamp member operatively engages the inner shaft, and wherein the inner shaft moves in at least one of a first direction and a second direction opposite the first direction;
 a mandrel comprising a tubular side wall extending longitudinally between a first end portion and a second end portion, the tubular side wall including an outer circumferential surface and an inner circumferential surface, wherein the mandrel substantially surrounds the inner shaft;
 a mount member having a proximal end portion and a distal end portion opposite the proximal end portion, wherein the proximal end portion of the mount member is configured to receive the second end portion of the mandrel, and wherein the mount member includes an internal cavity and defines an aperture;
 a block member positioned in the internal cavity of the mount member, wherein the distal end portion of the inner shaft is configured to engage with the block member;
 a bracing member slidably engaged with the block member and configured to protrude through the aperture of the mount member;
 a hub assembly adjacent to the mount member;
 wherein as the inner shaft moves longitudinally in a first direction, the distal end portion of the inner shaft engages the block member causing the bracing member to move radially outward to press against the inner circumferential surface of the mandrel;
 wherein as the inner shaft moves longitudinally in a second direction, the distal end portion of the inner shaft disengages the block member causing the bracing member to move radially inward to release the inner circumferential surface of the mandrel; and
 wherein the a clamp member comprises a plunger and a handle, wherein the plunger includes a distal end portion and a proximal end portion opposite the distal end portion, and wherein the handle is adjacent to the proximal end portion of the plunger.

15. The loading apparatus of claim 14, further comprising an outer shaft having an internal shaft surface and an external shaft surface opposite the internal shaft surface, wherein the inner shaft is slidably engaged with the internal shaft surface of the outer shaft.

16. The loading apparatus of claim 15, a wedge member slidably associated with the external shaft surface of the outer shaft.

17. The loading apparatus of claim 16, a gripping member slidably engaged with a portion of the wedge.

18. The loading apparatus of claim 14, further comprising a rod having a proximal end portion and a distal end portion opposite the proximal end portion, wherein the proximal end portion of the rod is operatively engaged with the distal end portion of the plunger.

19. The loading apparatus of claim 14, wherein an external surface of the wedge member includes at least one of a receiving key portion and a protruding key portion.

20. The loading apparatus of claim 14, further comprising a tension member adjacent to the block member.

21. The mandrel support apparatus of claim 14, further comprising an unwind arm having a distal end portion and a proximal end portion, and wherein the hub assembly is configured to rotate about the unwind arm.

22. The mandrel support apparatus of claim 14, further comprising a brake member disposed between the mount member and the hub assembly.

23. A method for loading a spool on an unwinding device, the method comprising the steps of:
   providing a mandrel comprising a tubular side wall extending longitudinally between a first end portion and a second end portion, the tubular side wall including an outer circumferential surface and an inner circumferential surface;
   retracting a gripping member radially inward through an aperture in the tubular side wall of the mandrel by moving a wedge member in a first direction longitudinally along the inner circumferential surface of the tubular side wall of the mandrel;
   providing a spool comprising a core and a web of material wound around the core;
   inserting the mandrel into the core;
   projecting the gripping member radially outward through the aperture in the tubular side wall of the mandrel to grip the core by moving a wedge member in a second direction longitudinally along the inner circumferential surface of the tubular side wall, wherein the second direction opposite the first direction;
   releasing the core by moving the wedge member longitudinally along the inner circumferential surface of the tubular side wall in the second direction;
   wherein at least one of the steps of retracting the gripping member and projecting the gripping member is accomplished by rotating a handle of a clamp member.

24. The method of claim 23, further comprising the step of connecting the mandrel to a mount member comprising an internal cavity and an aperture, wherein the internal cavity houses a block member and a bracing member.

25. The method of claim 24, further comprising the step of projecting the bracing member through the aperture of the mount member by moving the block member in a second direction.

26. The method of claim 24, further comprising the step of retracting the bracing member through the aperture of the mount member by moving the block member in a first direction opposite the second direction.

\* \* \* \* \*